(12) United States Patent
Smith, III

(10) Patent No.: US 6,491,928 B1
(45) Date of Patent: Dec. 10, 2002

(54) WATER-FLUX LIMITING CLEANSING ARTICLES

(75) Inventor: Edward Dewey Smith, III, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/487,916

(22) Filed: Jan. 19, 2000

Related U.S. Application Data

(60) Provisional application No. 60/116,565, filed on Jan. 21, 1999.

(51) Int. Cl.$^7$ .............................. A61K 7/00; A61K 9/70
(52) U.S. Cl. .................. 424/401; 424/400; 424/402; 424/404; 424/443; 252/92; 252/545
(58) Field of Search ................. 424/400, 402, 424/404, 286, 443, 407; 252/92, 545; 128/155

(56) References Cited

U.S. PATENT DOCUMENTS

| | | | |
|---|---|---|---|
| 3,283,357 A | 11/1966 | Decker et al. | 15/506 |
| 3,537,121 A | 11/1970 | McAvoy | 15/230.12 |
| 3,581,447 A | 6/1971 | Falivene | 51/400 |
| 3,597,299 A | 8/1971 | Thomas et al. | 161/57 |
| 3,896,807 A | 7/1975 | Buchalter | 128/261 |
| 3,910,284 A | 10/1975 | Orentreich | 128/355 |
| 4,189,395 A | 2/1980 | Bland | 252/91 |
| 4,287,633 A | 9/1981 | Gropper | 15/209 |
| 4,303,543 A | 12/1981 | Mansy | 252/117 |
| 4,515,703 A * | 5/1985 | Hag | 252/92 |
| 4,559,157 A | 12/1985 | Smith et al. | 252/90 |
| 4,569,343 A | 2/1986 | Kimura et al. | 128/155 |

(List continued on next page.)

FOREIGN PATENT DOCUMENTS

| | | | |
|---|---|---|---|
| BE | 855362 | 10/1977 | |
| CA | 810361 | 4/1969 | 15/121 |
| CN | 1050066 | 3/1991 | D21H/25/06 |
| EP | 0 211 664 | 2/1987 | A47L/13/17 |
| EP | 0 186 208 B1 | 5/1990 | C11D/17/04 |
| EP | 0 161 911 B1 | 8/1990 | C11D/17/04 |
| EP | 0 353 013 B1 | 9/1993 | A47L/13/17 |
| EP | 0 604 731 | 7/1994 | B32B/31/00 |

(List continued on next page.)

*Primary Examiner*—Thurman K. Page
*Assistant Examiner*—Rachel M. Bennett
(74) *Attorney, Agent, or Firm*—Armina E. Matthews; Dara M. Kendall; Tara M. Rosnell

(57) ABSTRACT

The present invention relates to a disposable cleansing article comprising:
a) a water insoluble substrate comprising:
  1) an apertured first layer wherein said first layer has a water flux rate of from about 0.4 cm$^3$/cm$^2$-s to about 20 cm$^3$/cm$^2$-s;
  2) a second layer attached to said first layer; and
b) a cleansing component comprising a surfactant, said component being disposed adjacent to the substrate.

The present invention also relates to a method of cleansing the skin and hair which comprise the steps of:
a) wetting with water a disposable cleansing article comprising a water insoluble substrate comprising:
  1) an apertured first layer having a water flux rate of from about 0.4 cm$^3$/cm$^2$-s to about 20 cm$^3$/cm$^2$-s; and
  2) a second layer attached to said first layer;
and a cleansing component comprising one or more surfactants said component being disposed adjacent to the substrate; and
b) contacting the skin or hair with the wetted article.

20 Claims, 2 Drawing Sheets

U.S. PATENT DOCUMENTS

| | | | |
|---|---|---|---|
| 4,600,620 A | 7/1986 | Lloyd et al. | 428/195 |
| 4,603,069 A | 7/1986 | Haq et al. | 428/76 |
| 4,629,643 A | 12/1986 | Curro et al. | 428/131 |
| 4,665,580 A | 5/1987 | Morris | 15/118 |
| 4,674,237 A | 6/1987 | Sullivan | 51/391 |
| 4,690,821 A | 9/1987 | Smith et al. | 424/401 |
| 4,735,739 A | 4/1988 | Floyd et al. | 252/91 |
| 4,758,467 A | 7/1988 | Lempiere | 428/290 |
| 4,769,022 A | 9/1988 | Chang et al. | 604/368 |
| 4,806,572 A | 2/1989 | Kellett | 521/112 |
| 4,820,435 A | 4/1989 | Zafiroglu | 252/90 |
| 4,891,227 A | 1/1990 | Thaman et al. | 424/443 |
| 4,931,201 A | 6/1990 | Julemont | 252/91 |
| 4,948,585 A | 8/1990 | Schlein | 424/404 |
| 5,139,841 A | 8/1992 | Makoui et al. | 428/109 |
| 5,156,843 A | 10/1992 | Leong et al. | 424/411 |
| 5,302,446 A | 4/1994 | Horn | 428/286 |
| 5,412,830 A | 5/1995 | Girardot et al. | 15/118 |
| 5,507,968 A | 4/1996 | Palaikis | 252/90 |
| 5,538,732 A | 7/1996 | Smith et al. | 424/402 |
| 5,605,749 A | 2/1997 | Pike et al. | 442/60 |
| 5,698,475 A | 12/1997 | Vlasblom | 442/59 |
| 5,702,992 A * | 12/1997 | Martin et al. | 442/123 |
| 5,756,112 A | 5/1998 | Mackey | 424/402 |
| 5,763,332 A | 6/1998 | Gordon et al. | 442/84 |

FOREIGN PATENT DOCUMENTS

| | | | |
|---|---|---|---|
| EP | 0 421 163 B1 | 11/1994 | C11D/17/04 |
| EP | 0 353 014 B1 | 1/1996 | A47L/13/17 |
| EP | 0 750 062 | 12/1996 | D04H/1/40 |
| EP | 0 836 842 | 5/1998 | A61F/13/15 |
| EP | 0 864 418 | 9/1998 | B32B/29/00 |
| EP | 0 870 496 | 10/1998 | A61K/7/50 |
| JP | 06-017361 | 1/1994 | D04H/1/54 |
| WO | WO 94/02674 | 2/1994 | D04H/13/00 |
| WO | WO-94/02674 A1 * | 2/1994 | |
| WO | WO 98/27257 | 6/1998 | D04H/1/00 |
| WO | WO-99/13861 A1 * | 3/1999 | |
| WO | WO 99/46119 | 9/1999 | B32B/27/14 |

* cited by examiner

WATER-FLUX LIMITING CLEANSING ARTICLES

CROSS REFERENCE TO RELATED APPLICATION

This application claims the benefit of U.S. provisional patent application Ser. No. 60/116,565, filed on Jan. 21, 1999.

TECHNICAL FIELD

The present invention relates to disposable, cleansing articles useful for cleansing the skin, hair and any other sites in need of cleansing. These articles comprise a water insoluble substrate having an apertured first and a second layer and a cleansing component disposed adjacent to the water insoluble substrate wherein the cleansing component comprises one or more surfactants. Consumers use the articles by wetting them with water and rubbing on the area to be cleansed.

The invention also encompasses methods for cleansing and conditioning the skin and hair, cleansing dishes and other hard surfaces using the articles of the present invention.

BACKGROUND OF THE INVENTION

Personal care products, particularly cleansing and conditioning products, have traditionally been marketed in a variety of forms such as bar soaps, creams, lotions, and gels. Typically, these products have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair overly dry after frequent use.

It is also highly desirable to deliver such cleansing and conditioning benefits from a disposable product. Disposable products are convenient-because they obviate the need to carry or store cumbersome bottles, bars, jars, tubes, and other forms of clutter including cleansing products and other products capable of providing therapeutic or aesthetic benefits. Disposable products are also a more sanitary alternative to the use of a sponge, washcloth, or other cleansing implement intended for extensive reuse, because such implements develop can bacterial growth, unpleasant odors, and other undesirable characteristics related to repeated use.

The articles of the present invention surprisingly provide effective cleansing as well as therapeutic or aesthetic benefits to the skin and hair in a convenient, inexpensive, and sanitary manner. The present invention provides the convenience of not needing to carry, store, or use both a separate cleansing implement (such as a washcloth or sponge) and a cleanser. The articles of the present invention can also provide a therapeutic or aesthetic benefit without the need for a separate benefit providing product. These articles are convenient to use because they are in the form of either a single, disposable personal care article or multiple disposable articles useful for cleansing as well as application of a therapeutic or aesthetic benefit agent. Moreover, these articles are suitable for use within or in conjunction with another cleansing implement which is designed for more extensive use. In this instance, the articles of the present invention are disposed within or attached to a separate cleansing implement which is not readily disposable, e.g., a bath towel or washcloth. In addition, the disposable articles of the present invention may be removeably attached to a handle or grip suitable for moving the article over the surface to be cleansed.

Although in preferred embodiments the articles of the present invention are suitable for personal care applications, they may be useful in a variety of other industries such as the automotive care, marine vehicle care, household care, dish care, animal care, etc. where surfaces or areas are in need of cleansing and/or application of a benefit agent, e.g., wax, conditioner, UV protectant, etc.

In preferred embodiments of the present invention, the articles are suitable for personal care applications and are useful for cleansing the skin, hair, and similar surfaces in need of cleansing. Consumers use these articles by wetting them with water and rubbing on the area to be cleansed. The article consists of a water insoluble substrate having a defined first layer and a second layer and a cleansing component containing a surfactant. Without being limited by theory, the substrate enhances lathering which in turn increases cleansing and exfoliation, and optimizes delivery and deposition of a therapeutic or aesthetic benefit agent which might be contained within the article.

SUMMARY OF THE INVENTION

The present invention relates to a disposable cleansing article comprising:
a) a water insoluble substrate comprising:
   1) an apertured first layer wherein said first layer has a water flux rate of from about 0.4 $cm^3/cm^2$-s to about 20 $cm^3/cm^2$-s;
   2) a second layer attached to said first layer; and
b) a cleansing component comprising one or more surfactants, said component disposed adjacent to said substrate.

The present invention also relates to a method of cleansing the skin and hair which comprises the steps of: a) wetting such articles with water and b) contacting the skin or hair with the wetted articles.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

All documents referred to herein, including patents, patent applications, and printed publications, are hereby incorporated by reference in their entirety in this disclosure.

DETAILED DESCRIPTION OF THE INVENTION

Figure 1:
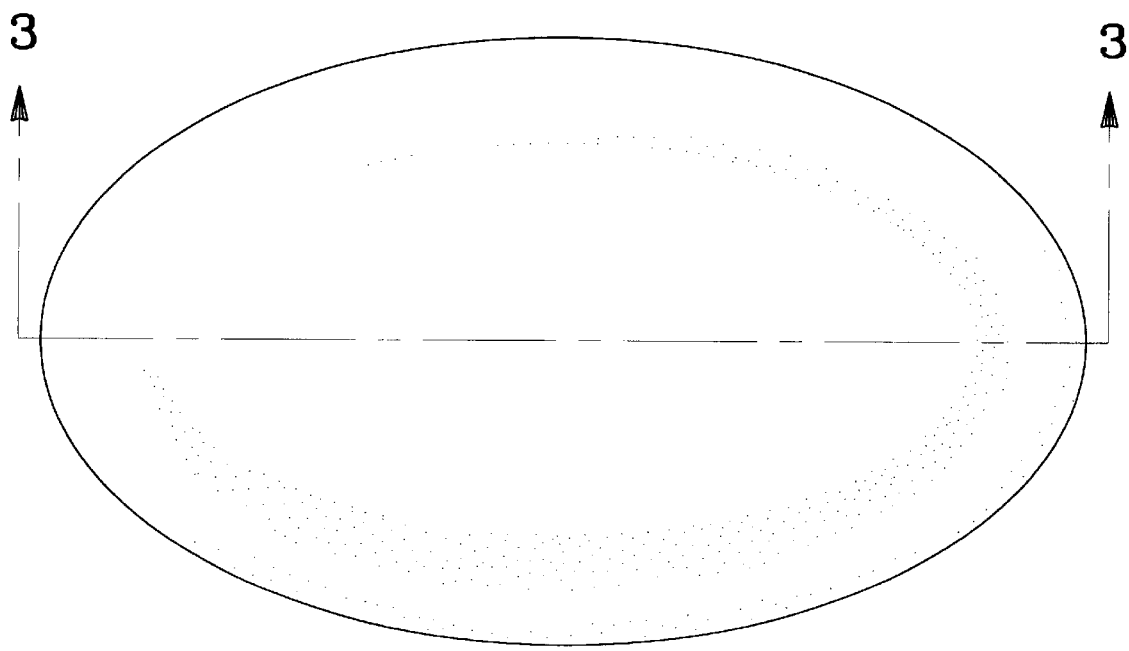
FIG. 1 is a plan view of an oval shaped embodiment of the present invention.
Figure 2:
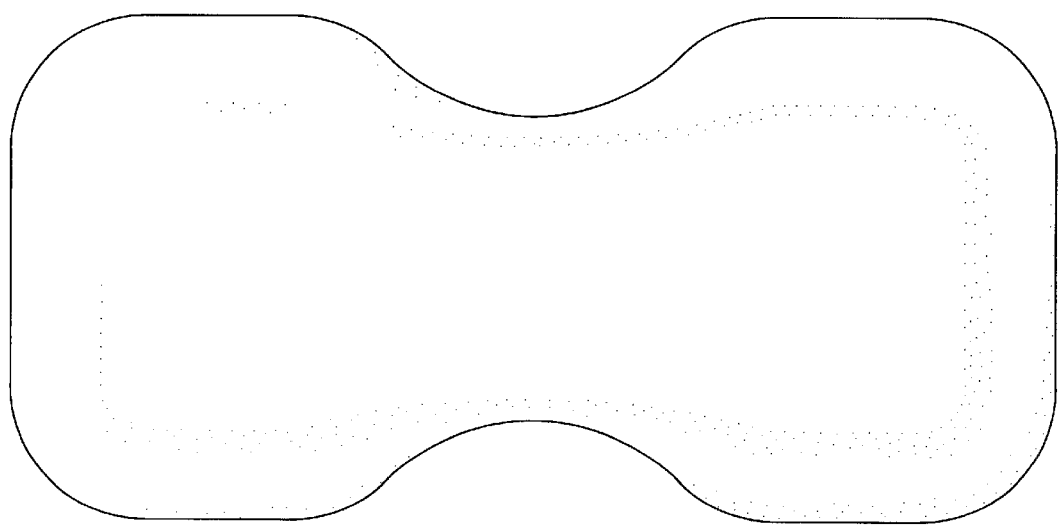
FIG. 2 is an alternative plan view of an hour glass shaped embodiment of the present invention.
Figure 3:
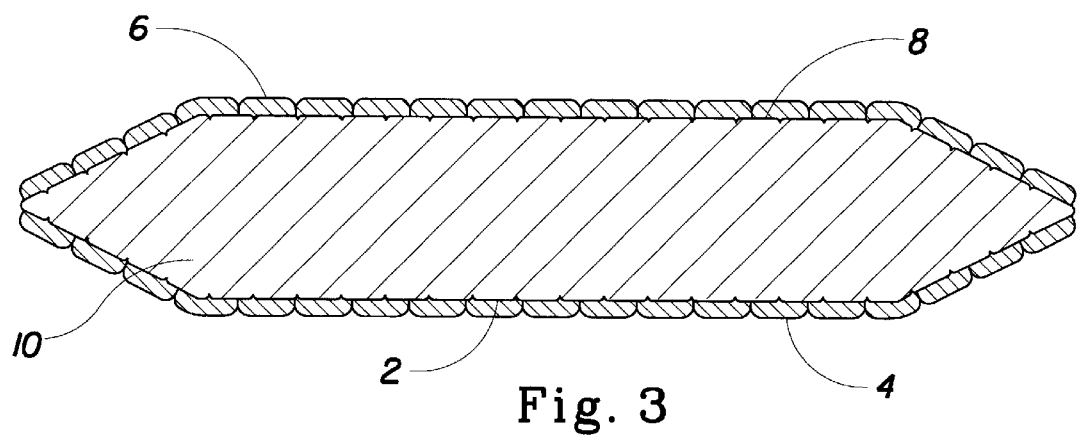
FIG. 3 is a cross section view of FIG. 1.

As used herein, "disposable" is used in its ordinary sense to mean an article that is disposed or discarded after a limited number of usage events, preferably less than 25, more preferably less than about 10, and most preferably less than about 2 entire usage events.

As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The determination of the Moisture Retention is discussed later.

The term "water-activated," as used herein, means that the present invention is presented to the consumer in dry form to be used after wetting with water. It is found that when the articles of the present invention include a lathering surfactant they produce a lather or are "activated" upon contact with water and further agitation.

The cleansing articles, particularly the personal care cleansing articles, of the present invention comprise the following essential components.

I. WATER INSOLUBLE SUBSTRATE

The articles of the present invention comprise a water insoluble substrate which further comprises at least two layers, namely an apertured first layer and a second layer which is attached to the first layer. Preferably, the substrate layers are soft to the skin of the consumer when used. In any case, however, the apertured first layer and the second layer are each defined as having both an interior and exterior surface. In both cases, the interior surfaces of the layers are those which face the inside or innermost portion of the article of the present invention whereas the exterior surfaces of the layers are those which face the outside or outermost portion of the article. Generally, the orientation of the articles of the present invention may be defined such that the apertured first layer is closer to the side of the article suitable for gripping (i.e., the gripping side) while the second layer is closer to the side of the article to be contacted with the area to be cleansed, e.g. the skin/site contact side.

Without being limited by theory, the water insoluble substrate enhances cleansing and therapeutic treatment. The substrate can have the same or differing textures on each side such that the gripping side of the article is the same or different texture as the skin/site contact side. The substrate may act as an efficient lathering and exfoliating implement. By physically coming into contact with the skin or hair, the substrate significantly aids in cleansing and removal of dirt, makeup, dead skin, and other debris. In preferred embodiments, however, the substrate is nonabrasive to the skin.

A. APERTURED FIRST LAYER

The apertured first layer 8 of the present invention has a water flux rate of from about 0.4 $cm^3/cm^2$-s to about 20 $cm^3/cm^2$-s, more preferably from about 1 $cm^3/cm^2$-s to about 5 $cm^3/cm^2$-s, even more preferably from about 1.5 $cm^3/cm^2$-s to about 4 $cm^3/cm^2$-s, and most preferably from about 2 $cm^3/cm^2$-s to about 3 $cm^3/cm^2$-s. The water flux rate may be determined using the method discussed below in the Properties section. As used herein, "apertured" means that the layer includes well-defined openings. Well-defined openings are typically surrounded by well-defined land areas. Also, as used herein, "apertures" encompasses holes, perforations, cavities, and the like. The well defined opening can be impermeable (as in a film, which would be a formed film or a perforated film, e.g.), or permeable. The apertures of the first layer are useful for enabling the passage of water flow through the material of the first layer. In one embodiment, the apertures of the present invention are characterized by the presence of petal-like edged surface aberrations which tend to add a three dimensional character to the layer.

Preferably, the first layer has at least about 1 aperature/$cm^2$. More preferably, the first layer has at least about 10 apertures/$cm^2$, even more preferably at least about 100 apertures/$cm^2$, even still more preferably at least about 500 apertures/$cm^2$, still more preferably at least about 1,000 apertures/$cm^2$, and most preferably at least about 1,500 apertures/$cm^2$.

The apertured first layer may comprise any apertured material which is well known in the art which exhibits the requisite water flux rate. Suitable materials include, but are not limited to, nonwovens, wovens, formed films, etc. Preferably, the apertured first layer comprises a plastic formed film. Preferred plastics include those which are soft to the skin including, but not limited to, polyolefins such as low density polyethylenes (LDPE) and the like.

In the present invention, a preferred embodiment includes an apertured first layer that is microapertured. As used herein, "microapertured" generally refers to layers containing well-defined microscopic apertures (i.e., those not readily visible to the naked eye having 20/20 vision). Preferably, the microapertures are characterized by the presence of petal-like edged surface aberrations on at least one surface of the layer which add a three dimensional character to the layer. On the other hand, "macroapertured", as used herein refers to a layer containing well-defined apertures having an average diameter of greater than about 300 microns. Preferably, the microapertures are characterized by the presence of petal-like edged surface aberrations on at least one surface of the layer such that the layer has a three dimensional character and such that fluid flow is facilitated from one surface of the layer to another surface of the layer. Suitable microapertured materials useful for the first layer of the present invention include, but are not limited to, those disclosed in co-pending application U.S. Ser. No. 08/326, 571 and PCT Application No. US95/07435, filed Jun. 12, 1995 and published Jan. 11, 1996 and U.S. Pat. No. 4,629, 643, issued on Dec. 16, 1986 to Curro et al., which are incorporated by reference herein in their entirety.

In another embodiment, the first layer of the present invention may comprise a composite material, i.e., a material having one or more plies of the same or different suitable materials merely superimposed physically, joined together continuously (e.g., laminated, etc.) in a discontinuous pattern, or by bonding at the external edges (or periphery) of the layer and/or at discrete loci. In this embodiment, the first layer is preferably selected from the group consisting of formed films and formed film composite materials. Furthermore, in this embodiment, the first layer may be a formed film composite material comprising at least one formed film and at least one nonwoven wherein the layer is vacuum formed. A suitable formed film composite material includes, but is not limited to, a vacuum laminated composite formed film material formed by combining a carded polypropylene nonwoven having a basis weight of 30 gsm with a formed film.

Without being limited by theory, the apertured first layer is useful for controlling water flux through the gripping side of the substrate of the article in order to provide controlled wetting and to extend the useful life of the cleansing component, namely the surfactant, such that it lasts through at least one shower or bathing or cleansing experience (window, car, bathroom surface, floor, dog, dishes, etc. experience. Impermeable substrate layers tend to completely prohibit or extremely limit water flux and therefore the cleansing component is often slow to wet or lather while highly permeable substrate layers tend to quickly release the cleansing component such that it is not present throughout an entire shower or bathing experience. Therefore, it is preferable that the a flux differential (or gradient) of at least 2.5 cm³/cm²-s is present between the first layer and second layer of the articles of the present invention. More preferably, a flux differential of at least 3.0 cm³/cm²-s, and most preferably at least 4.0 cm³/cm²-s exists between the first and second layers of the articles of the present invention.

B. SECOND LAYER

The water insoluble substrate of the present invention further comprises a second layer 2 attached to the first layer. This second layer may be useful for engaging or retaining the cleansing component within the article. Furthermore, the second layer may also be suitable for contact with the skin in which case it is preferred that the layer is soft to the skin. It also may be desirable for scrubbing counters, pots and pans, bathroom areas, etc.

Materials suitable for the second layer are selected from the group consisting of nonwovens, wovens, sponges (i.e., both natural and synthetic), polymeric netted meshes (also referred to herein as "scrims"), formed films, battings, and combinations thereof. Preferred embodiments of the second layer employ nonwovens. As used herein, "nonwoven" means that the layer comprises fibers which are not woven into a fabric but rather are formed into a sheet, mat, or pad layer. The fibers can either be random (i.e., randomly aligned) or they can be carded (i.e., combed to be oriented in primarily one direction). Furthermore, the nonwoven of the second layer can be a composite material composed of a combination of additional layers, i.e., plies, of random and carded fibers.

The nonwovens of the second layer may comprise a variety of both natural and synthetic materials. As used herein, "natural" means that the materials are derived from plants, animals, insects or byproducts of plants, animals, and insects. As used herein, "synthetic" means that the materials are obtained primarily from various man-made materials or from natural materials which have been further altered. The conventional base starting material is usually a fibrous web comprising any of the common synthetic or natural textile-length fibers, or combinations thereof.

Nonlimiting examples of natural materials useful in the present invention include, but are not limited to, silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and combinations thereof. Cellulosic fiber materials are preferred in the present invention.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyethylene foam, polyurethane foam, and combinations thereof. Examples of suitable synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and combinations thereof. These and other suitable fibers and the nonwovens prepared therefrom are generally described in Riedel, "Nonwoven Bonding Methods and Materials," *Nonwoven World* (1987); *The Encyclopedia Americana*, vol. 11, pp. 147–153, and vol. 26, pp. 566–581 (1984); U.S. Pat. No. 4,891,227, to Thaman et al., Jan. 2, 1990; and U.S. Pat. No. 4,891,228, each of which is incorporated by reference herein in its entirety.

A preferred nonwoven second layer comprises batting which comprises synthetic fibers. Preferred synthetic fibers may be selected from the group consisting of nylon fibers, rayon fibers, polyolefin fibers, polyester fibers, and combinations thereof. Preferred polyolefin fibers are fibers selected from the group consisting of polyethylene, polypropylene, polybutylene, polypentene, and combinations and copolymers thereof. More preferred polyolefin fibers are fibers selected from the group consisting of polyethylene, polypropylene, and combinations and copolymers thereof. Preferred polyester fibers are fibers selected from the group consisting of polyethylene terephthalate, polybutylene terephthalate, polycyclohexylenedimethylene terephthalate, and combinations and copolymers thereof. More preferred polyester fibers are fibers selected from the group consisting of polyethylene terephthalate, polybutylene terephthalate, and combinations and copolymers thereof. Most preferred synthetic fibers comprise solid staple polyester fibers which comprise polyethylene terephthalate homopolymers. Suitable synthetic materials may include solid single component (i.e., chemically homogeneous) fibers, multiconstituent fibers (i.e., more than one type of material making up each fiber), and multicomponent fibers (i.e., synthetic fibers which comprise two or more distinct filament types which are somehow intertwined to produce a larger fiber), and combinations thereof. Preferred fibers include bicomponent fibers, multiconstituent fibers, and combinations thereof. Such bicomponent fibers may have a core-sheath configuration or a side-by-side configuration. In either instance, the nonwoven layer may comprise either a combination of fibers comprising the above-listed materials or fibers which themselves comprise a combination of the above-listed materials.

For the core-sheath fibers, preferably, the cores comprise materials selected from the group consisting of polyesters, polyolefins having a $T_g$ of at least about 10° C. higher than the sheath material, and combinations thereof. Conversely, the sheaths of the bicomponent fibers preferably comprise materials selected from the group consisting of polyolefins having a $T_g$ of at least about 10° C. lower than the core material, polyesters polyolefins having a $T_g$ of at least about 10° C. lower than the core material, and combinations thereof.

In any instance, side-by side configuration, core-sheath configuration, or solid single component configuration, the fibers of the nonwoven first layer may exhibit a helical or spiral or crimped configuration, particularly the bicomponent type fibers.

Polymeric nets (referred to herein as a "scrim" materials) are also useful herein as materials for the second layer are described in detail in U.S. Pat. No. 4,636,419, which is incorporated by reference herein. The scrim materials can be formed directly at the extrusion die or can be derived from extruded films by fibrillation or by embossing, followed by stretching and splitting. The scrim can be derived from a polyolefin such as polyethylene or polypropylene, copolymers thereof, poly(butylene terephthalate), polyethylene terephthalate, Nylon 6, Nylon 66, and the like. Furthermore, the scrim materials can be multiconstituent (i.e., made up of more than one material), multicomponent (i.e., a material which includes at least two filament types). Scrim materials are available from various commercial sources. A preferred scrim material useful in the present invention is a polypropylene scrim, available from Conwed Plastics (Minneapolis, Minn.). Another preferred scrim material is a polyethylene scrim, particularly a low density polyethylene, which is also available from Conwed.

In another aspect of the present invention, Applicants have also discovered that the incorporation of a scrim material into the apertured first layer or second layer, followed by heating, provides macroscopic three-dimensional character to the article. This macroscopic three-dimensionality has been found to greatly enhance cleansing performance of the article, even where the basis weight of the sheet is essentially uniform. In particular, macroscopic three-dimensionality is achieved when the scrim/fiber composite is subjected to heating, then cooling. This process results in shrinkage (in the X-Y dimension) of the scrim and, as a result of its being attached with the fibers, provides a sheet with greater three-dimensionality. As used herein, the term "X-Y dimension" refers to the plane orthogonal to the thickness of the layer, ply, or article, or a component thereof. The X and Y dimensions usually correspond to the length and width, respectively, of the sheet or a sheet component. As used herein, the term "Z-dimension" refers to the dimension orthogonal to the length and width of the cleaning sheet of the present invention, or a component thereof. The Z-dimension usually corresponds to the thickness of the sheet.

The degree of added three-dimensionality is controlled by the level of shrinking of (e.g., by heating) the scrim/cleaning combination. The inclusion of a scrim is particularly beneficial when the fiber aspect of the structure is a nonwoven, particularly when the structure is hydroentangled. Further detail of suitable scrim material containing nonwovens may be found in copending U.S. application Ser. Nos. 09/082,396 and 09/082,349, both filed on May 20, 1998, by Fereshtehkho et al., which are incorporated by reference herein in their entirety.

Additional nonwovens suitable for the second layer may be made from natural materials consist of webs or sheets most commonly formed on a fine wire screen from a liquid suspension of the fibers. See C. A. Hampel et al., *The Encyclopedia of Chemistry*, third edition, 1973, pp. 793–795 (1973); *The Encyclopedia Americana*, vol. 21, pp. 376–383 (1984); and G. A. Smook, *Handbook of Pulp and Paper Technologies*, Technical Association for the Pulp and Paper Industry (1986); which are incorporated by reference herein in their entirety.

Natural material nonwovens useful for the second layer of the present invention may be obtained from a wide variety of commercial sources. Nonlimiting examples of suitable commercially available paper layers useful herein include Airtex®, an embossed airlaid cellulosic layer having a base weight of about 71 gsy, available from James River, Green Bay, Wis.; and Walkisoft®, an embossed airlaid cellulosic having a base weight of about 75 gsy, available from Walkisoft U.S.A., Mount Holly, N.C.

Additional suitable nonwoven materials include, but are not limited to, those disclosed in U.S. Pat. No. 4,447,294, issued to Osborn on May 8, 1984; U.S. Pat. No. 4,603,176 issued to Bjorkquist on Jul. 29, 1986; U.S. Pat. No. 4,981,557 issued to Bjorkquist on Jan. 1, 1991; U.S. Pat. No. 5,085,736 issued to Bjorkquist on Feb. 4, 1992; U.S. Pat. No. 5,138,002 issued to Bjorkquist on Aug. 8, 1992; 5,262,007 issued to Phan et al. on Nov. 16, 1993; U.S. Pat. No. 5,264,082, issued to Phan et al. on Nov. 23, 1993; U.S. Pat. No. 4,637,859 issued to Trokhan on Jan. 20, 1987; U.S. Pat. No. 4,529,480 issued to Trokhan on Jul. 16, 1985; U.S. Pat. No. 4,687,153 issued to McNeil on Aug. 18, 1987; U.S. Pat. No. 5,223,096 issued to Phan et al. on Jun. 29, 1993 and U.S. Pat. No. 5,679,222, issued to Rasch et al. on Oct. 21, 1997, each of which is incorporated by reference herein in its entirety.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including, but not limited to, hydroentanglement, thermally bonding or thermo-bonding, and combinations of these processes.

Nonwovens made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novonet® 149-616, a thermo-bonded grid patterned material containing about 100% polypropylene, and having a basis weight of about 50 gsy, available from Veratec, Inc., Walpole, Mass.; Novonet® 149-801, a thermo-bonded grid patterned material containing about 69% rayon, about 25% polypropylene, and about 6% cotton, and having a basis weight of about 75 gsy, available from Veratec, Inc. Walpole, Mass.; Novonet® 149-191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee, New Brunswick, N.J.; Keybak® 1368, an apertured material, containing about 75% rayon, about 25% polyester, and having a basis weight of about 39 gsy, available from Chicopee, New Brunswick, N.J.; Duralace® 1236, an apertured, hydroentangled material, containing about 100% rayon, and having a basis weight from about 40 gsy to about 115 gsy, available from Chicopee, New Brunswick, N.J.; Duralace® 5904, an apertured, hydroentangled material, containing about 100% polyester, and having a basis weight from about 40 gsy to about 115 gsy, available from Chicopee, New Brunswick, N.J.; Sontaro 8868, a hydroentangled material, containing about 50% cellulose and about 50% polyester, and having a basis weight of about 60 gsy, available from Dupont Chemical Corp.

The second layer may also be a polymeric mesh sponge as described in European Patent Application No. EP 702550A1 published Mar. 27, 1996, which is incorporated by reference herein in its entirety. Such polymeric mesh sponges comprise a plurality of plies of an extruded tubular netting mesh prepared from a strong flexible polymer, such as addition polymers of olefin monomers and polyamides of polycarboxylic acids.

The second layer may also be made from formed films and composite materials, i.e., multiply materials containing formed films. Preferably, such formed films comprise plastics which tend to be soft to the skin. Suitable soft plastic formed films include, but are not limited to, polyolefins such as low density polyethylenes (LDPE). In such cases where the second layer comprises a plastic formed film, it is preferred that the second layer be apertured, e.g., macroapertured or microapertured. Preferably, the second layer comprises a plastic formed film which is only microapertured. The surface aberrations of the microapertures, i.e., the male side, are preferably located on the interior surface of the second layer and preferably face toward the inside of the substrate, i.e., toward the cleansing component. In preferred embodiments which include apertures having petal-like edged surface aberrations, without being limited by theory, it is believed that when the surface aberrations of the apertures face toward the surfactant-containing cleansing component, the application of pressure by the hand to the article allows the petal-like edges of the surface aberrations to fold inward thereby creating numerous valves on the interior surface of the layer which in effect meter out the cleansing component contained within the article thereby extending the article's useful life.

In a more preferred embodiment, the second layer comprises a plastic formed film which is both microapertured and macroapertured. In such embodiments, the second layer is well-suited to contact the area to be cleansed given the cloth-like feel of such microapertured films. Preferably, in such an embodiment, the surface aberrations of the microapertures face opposite of the surface aberrations of the macroapertures on the second layer. In such an instance, it is believed that the macroapertures maximize the overall wetting/lathering of the article by the three-dimensional thickness formed from the surface aberrations which are under constant compression and decompression during the use of the article thereby creating lathering bellows.

In certain embodiments of the present invention the second layer is apertured. In such instances it is preferred that the second layer have at least about 1 aperature/cm$^2$. More preferably, the second layer has at least about 10 apertures/cm$^2$, even more preferably at least about 100 apertures/cm$^2$, even still more preferably at least about 500 apertures/cm$^2$, still more preferably at least about 1,000 apertures/cm$^2$, and most preferably at least about 1,500 apertures/cm$^2$.

More preferred embodiments of the present invention include a second layer which has water flux rate of from about 5 cm$^3$/cm$^2$-s to about 120 cm$^3$/cm$^2$-s, more preferably from about 10 cm$^3$/cm$^2$-s to about 90 cm$^3$/cm$^2$-s, even more preferably from about 10 cm$^3$/cm$^2$-s to about 50 cm$^3$/cm$^2$-s, and most preferably from about 15 cm$^3$/cm$^2$-s to about 40 cm$^3$/cm$^2$-s.

Suitable formed films and formed film-containing composite materials useful in the second layer of the present invention include, but are not limited to, those disclosed in U.S. Pat. No. 4,342,314 issued to Radel et al. on Aug. 3, 1982, commonly assigned co-pending application U.S. Serial No. 08/326,571 and PCT Application No. US95/07435, filed Jun. 12, 1995 and published Jan. 11, 1996, and U.S. Pat. No. 4,629,643, issued to Curro et al. on Dec. 16, 1986, each of which is incorporated by reference herein in its entirety. Additional materials suitable for use in the second layer include those selected from the group consisting of formed films and formed film composite materials. Furthermore, the second layer may be a formed film composite material comprising at least one formed film and at least one nonwoven wherein the layer is vacuum formed. A suitable formed film composite material includes, but is not limited to, a vacuum laminated composite formed film material formed by combining a carded polypropylene nonwoven having a basis weight of 30 gsm with a formed film.

II. CLEANSING COMPONENT

The articles of the present invention comprise a cleansing component 10 which further comprises one or more surfactants. The cleansing component is disposed between the first layer and second layer of the water insoluble substrate. The articles of the present invention comprise from about 0.5% to about 3,000% preferably from about 50% to about 2,000%, and more preferably from about 100% to about 1,500%, based on the weight of the water insoluble substrate, of the surfactant. Also, the articles of the present invention preferably comprise at least about 1 gram, by weight of the water insoluble substrate, of a surfactant. Thus, the cleansing component may be added to the substrate without requiring a drying process.

The surfactants of the cleansing component may be lathering or non-lathering surfactants. As used herein, "lathering surfactant" means a surfactant, which when combined with water and mechanically agitated generates a foam or lather. It is preferred, however, that the surfactants be lathering since increased lather is important to consumers as an indication of cleansing effectiveness. In certain embodiments, the surfactants or combinations of surfactants should be mild. As used herein, "mild" means that the surfactants as well as to the articles of the present invention demonstrate skin mildness comparable to a mild alkyl glyceryl ether sulfonate (AGS) surfactant based synthetic bar, i.e., synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water (3H—H$_2$O) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

A wide variety of lathering surfactants are useful herein and include those selected from the group consisting of anionic lathering surfactants, nonionic lathering surfactants, cationic lathering surfactants, amphoteric lathering surfactants, and mixtures thereof.

Anionic Lathering Surfactants

Nonlimiting examples of anionic lathering surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975, each of which is incorporated by reference herein in their entirety.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention.

Anionic surfactants for use in the cleansing component include alkyl and alkyl ether sulfates. These materials have the respective formulae $R1O—SO3M$ and $R1(CH2H4O)x—O—SO3M$, wherein R1 is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the cleansing component are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R1CO—O—CH2—C(OH)H—CH2—O—SO3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R1SO3M$, wherein R1 is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium C14/C16 alpha olefin sulfonate.

Other suitable anionic surfactants are the linear alkylbenzene sulfonates of the form $R1—C6H4—SO3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing component include the primary or secondary alkane sulfonates of the form $R1SO3M$, wherein R1 is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium C13–C17 paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate as detailed in U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable for use in the cleansing component is the acyl isethionates. The acyl isethionates typically have the formula $R1CO—O—CH2CH2SO3M$ wherein R1 is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R1—OCH2—C(OH)H—CH2—SO3M$, wherein R1 is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R1—CH(SO4)—COOH$ and sulfonated methyl esters of the from $R1—CH(SO4)—CO—O—CH3$, where R1 is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula R1CO—N(COOH)—CH2CH2—CO2M wherein R1 is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula R1CON(CH3)—CH2CH2—CO2M wherein R1 is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula R1—(OCH2CH2)x—OCH2—CO2M wherein R1 is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula R1CO—[O—CH(CH3)—CO]x—CO2M wherein R1 is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Other anionic materials include natural soaps derived from the saponification of vegetable and/or animal fats & oils exmaples of which include sodium laurate, sodium myristate, palmitate, stearate, tallowate, cocoate.

Any counter cation, M, can be used on the anionic surfactant. Preferably, the counter cation is selected from the group consisting of sodium, potassium, ammonium, monoethanolamine, diethanolamine, and triethanolamine. More preferably, the counter cation is ammonium.

Nonionic Lathering Surfactants

Nonlimiting examples of nonionic lathering surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g., C8–30 alcohols, with sugars or starches or sugar or starch polymers, i.e., glycosides or polyglycosides. These compounds can be represented by the formula (S)n—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein $R^1$ is H, $C_1$–$C_4$ alkyl, 2-hydroxyethyl, 2-hydroxypropyl, preferably $C^1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; each of which are incorporated herein by reference in their entirety.

Other examples of nonionic surfactants include amine oxides. Amine oxides correspond to the general formula $R_1R_2R_3N \rightarrow O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyldecylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Cationic Lathering Surfactants

Cationic lathering surfactants are also useful in the articles of the present invention. Suitable cationic lathering surfactants include, but are not limited to, fatty amines, di-fatty quaternary amines, tri-fatty quaternary amines, imidazolinium quaternary amines, and combinations thereof. Suitable fatty amines include monoalkyl quaternary amines such as cetyltrimethylammonium bromide. A suitable quaternary amine is dialklamidoethyl hydroxyethylmonium methosulfate. The fatty amines, however, are preferred. It is preferred that a lather booster is used when the cationic lathering surfactant is the primary lathering surfactant of the cleansing component. Additionally, nonionic surfactants have been found to be particularly useful in combination with such cationic lathering surfactants.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkylirinoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

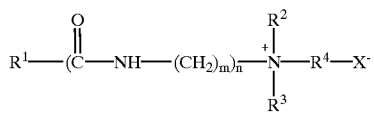

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

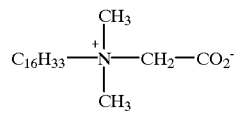

Cocamidopropylbetaine

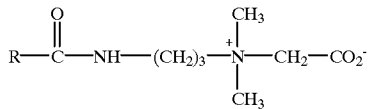

wherein R has from about 9 to about 13 carbon atoms

Cocamidopropyl hydroxy sultaine

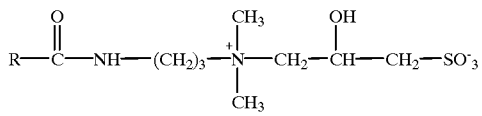

wherein R has from about 9 to about 13 carbon atoms,

Examples of other useful amphoteric surfactants are alkyliminoacetates, and iminodialkanoates and aminoalkanoates of the formulas RN[CH$_2$)$_m$CO$_2$M]$_2$ and RNH(CH$_2$)$_m$CO$_2$M wherein m is from 1 to 4, R is a C$_8$–C$_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants are selected from the group consisting of anionic lathering surfactants selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium monolauryl phospate, sodium cocoglyceryl ether sulfonate, sodium $C_9$–$C_{22}$ soap, and combinations thereof; nonionic lathering surfactants selected from the group consisting of lauramine oxide, cocoamine oxide, decyl polyglucose, lauryl polyglucose, sucrose cocoate, C12–14 glucosamides, sucrose laurate, and combinations thereof; cationic lathering surfactants selected from the group consisting of fatty amines, di-fatty quaternary amines, tri-fatty quaternary amines, imidazolinium quaternary amines, and combinations thereof, amphoteric lathering surfactants selected from the group consisting of disodium lauroamphodiacetate, sodium lauroamphoacetate, cetyl dimethyl betaine, cocoamidopropyl betaine, cocoamidopropyl hydroxy sultaine, and combinations thereof.

III. ADDITIONAL LAYERS

In a preferred embodiment, the article of the present invention comprises one or more additional layers (4, 6) which one having ordinary skill in the art would recognize as separate and distinct from the first and second layers yet which are attached to the first and second layers at some point. The additional layers are suitable for enhancing the overall grippability of the side of the article closest to the hand or other means for exerting mechanical action on the surface to be cleansed. Also, the additional layers may be suitable for enhancing either the soft feel or scrubbing efficacy of the side of the article which contacts the area to be cleansed. In any instance, these additional layers may also be referred to as consecutively numbered layers in addition to the two essential layers of the articles of the present invention, e.g., third layer, fourth layer, etc.

In a preferred embodiment, at least one additional layer, the third layer, is positioned adjacently to the exterior surface of the first layer such that it forms the outermost portion of the article. In this capacity, the third layer is useful for providing a surface suitable for facilitated gripping of the article by the hand. It is therefore desirable that when the third layer is positioned adjacently to the exterior surface of the first layer, the third layer exhibits a higher wet friction coefficient relative to the other layers of the article. In this embodiment, the third layer preferably has a Wet Friction Coefficient of greater than about 0.45, more preferably greater than about 0.55, and most preferably greater than 0.65. The Wet Friction Coefficient may be determined using the method discussed below in the Properties section. Furthermore, the third layer is preferably fluid permeable and soft to the skin. In another embodiment, the article comprises a fourth layer which is disposed adjacent to the second layer wherein the fourth layer comprises the same or different materials of the third layer.

Suitable materials useful for the additional layer include those disclosed above for both the first and second layers. Preferably, the materials of the additional layer are selected from the group consisting of nonwovens, wovens, sponges, polymeric netted meshes, formed films, battings, and combinations thereof. More preferably, the additional layer is a material selected from the group consisting of nonwovens, formed films, and combinations thereof. Even more preferably, the additional layers are selected from the group consisting of cellulosic fibers, synthetic fibers, formed films, and combinations thereof. Most preferably, the additional layers are selected from the group consisting of cellulosic fibers, synthetic fibers, and combinations thereof. In preferred embodiments, the additional layers may be composite materials such that they each consist of one or more plies, each ply being made from the same or different materials than the other plies.

In a particularly preferred embodiment, the additional layers of the articles of the present invention have a thickness of at least one millimeter. In this case, the additional layers are useful for engaging the cleansing component within the article of the present invention once pressure is applied via agitation of the article. In this preferred embodiment, the additional layers having a thickness of at least one millimeter provide structural support for the article such that its original shape is maintained throughout its useful life and the layer also tend to enhance the softness perception to the consumer.

Materials suitable for use in the additional layer having a thickness of at least one millimeter may include, but are not limited to, foam, sponge (i.e., both natural and synthetic), corrugated materials, macroscopically expanded materials, and combinations thereof. When the additional layer is macroscopically expanded, it is preferably selected from the group consisting of embossed materials, debossed materials, and combinations thereof.

As used herein, "macroscopically expanded, refers to webs, ribbons, and films which have been caused to conform to the surface of a three-dimensional forming structure so that both surfaces thereof exhibit a three-dimensional forming pattern of surface aberrations corresponding to the macroscopic cross-section of the forming structure, wherein the surface aberrations comprising the pattern are individually discernible to the normal naked eye (i.e., normal naked eye having 20/20 vision) when the perpendicular distance between the viewer's eye and the plane of the web is about 12 inches.

As used herein, "embossed" it is meant that the forming structure of the material exhibits a pattern comprised primarily of male projections. On the other hand, "debossed" refers to when the forming structure of the material exhibits a pattern comprised primarily of female capillary networks.

Materials suitable for use in the additional layer having a thickness of at least one millimeter include, but are not limited to, those web materials disclosed in U.S. Pat. No. 5,518,801, issued to Chappell et al. on May 21, 1996, which is incorporated by reference herein in its entirety.

Additional materials that are suitable for use as the additional layers of the present invention include the cellulosic nonwovens described in U.S. Pat. No. 4,447,294, the formed films of U.S. Pat. Nos. 4,342,314 and 4,629,643.

Each of the layers discussed herein comprises at least two surfaces, namely an interior surface and an exterior surface, each of which may have the same or different texture and abrasiveness. Preferably, the articles of the present invention comprise substrates and therefore layers which are soft to the skin. However, differing texture substrates can result from the use of different combinations of materials or from the use of different manufacturing processes or a combination thereof. For instance, a dual textured water insoluble substrate can be made to provide a cleansing article with the advantage of having a more abrasive side for exfoliation and a softer, absorbent side for gentle cleansing. In addition, the separate layers of the substrate can be manufactured to have different colors, thereby helping the user to further distinguish the surfaces.

Furthermore, each of the layers of the articles as well as the articles of the present invention may be made into a wide variety of shapes and forms including flat pads, thick pads, thin sheets, ball-shaped implements, irregularly shaped implements. The exact size of the layers will depend upon the desired use and characteristics of the article and may range in surface area size from about a square inch to about hundreds of square inches. Especially convenient layer and article shapes include, but are not limited to, square, circular, rectangular, hourglass, or oval shapes having a surface area of from about 5 in$^2$ to about 200 in$^2$, preferably from about 6 in$^2$ to about 120 in$^2$, and more preferably from about 15 in$^2$ to about 100 in$^2$, and a thickness of from about 0.5 mm to about 50 mm, preferably from about 1 mm to about 25 mm, and more preferably from about 2 mm to about 20 mm.

MULTIPLE ARTICLE EMBODIMENT

The article of the present invention may also be packaged with one or more articles suitable for providing separate benefits, e.g., aesthetic, therapeutic, functional, or otherwise, thereby forming a cleansing kit suitable for personal care use, automotive care use, household care use, dish care use, etc. The additional article of this cleansing kit preferably comprises a water insoluble substrate comprising at least one layer and a benefit agent component disposed adjacent to the substrate of the additional article. In another preferred embodiment the benefit agent component 5 may be added onto or impregnated into the substrate of the additional article. The benefit agent component of the additional article is suitable for providing therapeutic or aesthetic skin or hair benefits by deposition onto such surfaces of various agents including, but not limited to, conditioning agents, anti-acne actives, anti-wrinkle actives, anti-microbial actives, anti-fungal actives, anti-inflammatory actives, topical anesthetic actives, artificial tanning agents and accelerators, sunscreen actives, anti-oxidants, skin exfoliating agents, and combinations thereof.

The additional article of the present invention may also serve a functional benefit in addition to or in lieu of a therapeutic or aesthetic benefit. For instance, the additional article may be useful as a drying implement suitable for use to aid in the removal of water from the skin or hair upon completion of a showering or bathing experience.

MULTIPLE CHAMBERED EMBODIMENT

Figure 4:
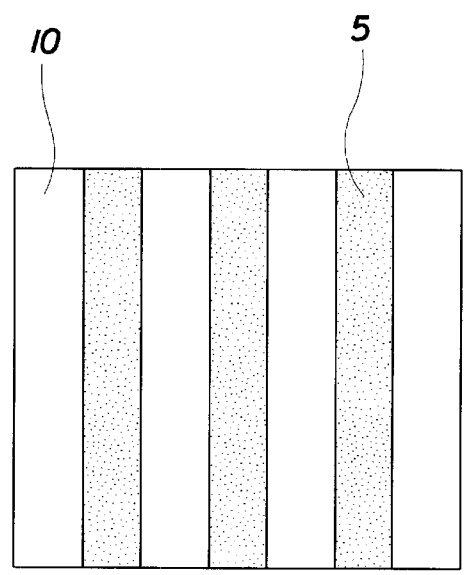
FIGS. 4 and 5 illustrate possible positions of the cleansing component in relation to a benefit agent in the multiple chambered embodiment of the article of the present invention.
Figure 5:
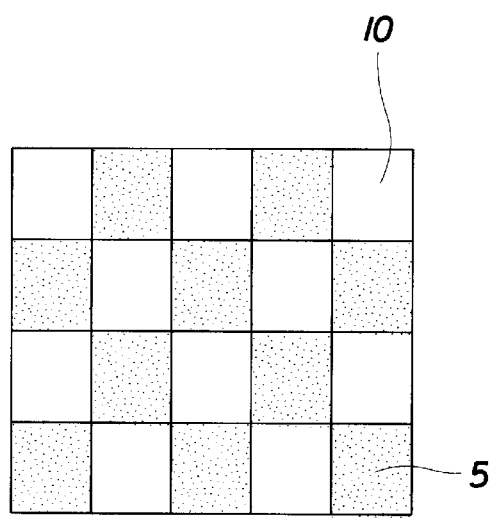

The article of the present invention may also comprise one or more chambers as illustrated in FIGS. 4 and 5. Such chambers or compartments result from the connection (e.g., bonding) of the substrate layers to one another at various loci to define enclosed areas. These chambers are useful, e.g., for separating various article components from one another, e.g., surfactant-containing cleansing component from conditioning agent. The separated article components which provide a therapeutic or aesthetic or cleansing benefit may be released from the chambers in a variety of ways including, but not limited to, solubilization, emulsification, mechanical transfer, puncturing, popping, bursting, squeezing of the chamber or even peeling away a substrate layer which composes a portion of the chamber.

PROPERTIES OF ARTICLE COMPONENTS

The articles of the present invention exhibit specific physical properties as defined by the Water Flux Rate Test, the Wet Friction Coefficient Test, the Foamability Test, the Absorptive Capacity Test (when an aqueous gel is present), and the Moisture Retention Methodology. These methods are described below.

Water Flux Rate Test

The Water Flux Rate Test measures the water permeability of a substrate. Without intending to be limited by theory, water permeability can be a principal determinant of surfactant longevity in a lathering substrate that is used in the presence of water, especially running water. When a lathering surfactant is present, it is desirable for it to lather quickly and profusely, yet be fully depleted at an intended time to signal disposability of the used substrate. If water permeability is too low, e.g. zero or near zero, insufficient wetting of the surfactant contained in the substrate can cause lather to start too slowly. On the other hand, if water permeability is too high, surfactant can be too readily flushed from the substrate, and the cleansing component containing the surfactant will not last throughout an entire cleansing experience.

In order to measure the Water Flux Rate, with tape or rubber bands, affix a substrate to the bottom of a plastic funnel with the following measurements: a 24 mm inner diameter (i.d.) at the exit, a 145 mm i.d. at the top, 135 mm height, a 20 mm length neck, and a total volume of about 600 ml. Apply sufficient tension to the substrate to ensure that the substrate is completely flat, and no more. Affix tape and rubber bands as close as possible to the exit of the funnel to keep backflow from occurring under water pressure. Next, place the throttled funnel in a ringstand over a sink. Measure out 600 ml of water at room temperature in a graduated cylinder. Then, with one hand blocking the funnel exit, pushing against the test substrate, quickly pour the water into the funnel. Once the funnel is completely filled, remove the hand and measure the drainage time for the water to evacuate the funnel to the nearest tenth of a second. Stop timing when the water reaches the junction of the neck and the sloped portion of the funnel. Repeat this process 5 times per test substrate and average the measurements for each substrate. Substrates which exhibit long drainage times (>10 minutes) can be tested by weighing the water drained in a set time period, e.g., 5 minutes, with a funnel full of water. Then remove the substrate from the funnel and reverse the substrate to the other side and reattach to funnel's exit. Measure the water flux rate in the opposite direction (unless the substrate is the same in both directions), and the average the results. The Water Flux Rate is expressed in cm$^3$/cm$^2$-s according to the following equation:

$$\text{Water Flux Rate} = (600 \text{ grams water}) \times (1 \text{ cm}^3 \text{ per gram}) / \{(\pi)(1.2 \text{ cm})^2 (\text{average time in seconds})\}$$

The apertured first layer of the articles of the invention are characterized by having a Water Flux Rate of from about 0.4 cm$^3$/cm$^2$-s to about 20 cm$^3$/cm$^2$-s, more preferably from about 1 cm$^3$/cm$^2$-s to about 5 cm$^3$/cm$^2$-s, even still more preferably from about 1.5 cm$^3$/cm$^2$-s to about 4 cm$^3$/cm$^2$-s an most preferably from about 2 cm$^3$/cm$^2$-s to about 3 cm$^3$/cm$^2$-s.

Wet Friction Coefficient Test

The Wet Friction Coefficient Test simulates wet conditions experienced in a shower or bath while it measures the resistance to sliding for a material against an in vitro skin analog under wet conditions. Without intending to be limited by theory, it is desirable that the side of the substrate moving against skin not exhibit a friction that is so low such that it has a slick and slippery feel on the skin similar to a bar of soap rather than like a cloth. It is also desirable that a substrate not exhibit a friction that is too high such that it feels draggy and difficult to move on the skin. On the other hand, the side of the substrate that is against the washing hand, in the absence of a grip or strap, should ideally exhibit a relatively higher wet friction coefficient to aid in the grippability of the article during cleansing.

The Wet Friction Coefficient may be measured using an Instron Model 1122 with Tensile Load Cell B (maximum range 2,000 gram) at a velocity of 5 inches/minute over a 5 inch (1 minute duration) area of the substrate. Use a 1.5 inch diameter, low friction pulley with a thin test string attached at each end to a sled and the Tensile Load Cell B to translate the Instron vertical motion into the horizontal motion of the sled. Attach the pulley to a very heavy base plate (e.g. 10 lbs). Next, sit a sled which weighs 145.5 grams and measures 9.5 cm×5.5 cm and has rounded edges on a sheet of skin-textured bioskin, 7.625 inches long by 5.125 inches wide and 0.2 inches thick, available in sheets from Beaulax Co., Ltd., Japan. Position a layer of 0.5 cm thick flexible polyurethane foam (104 gsm basis weight open cell foam) under the bioskin.

In order to run the Wet Friction Coefficient Test, attach a substrate to the sled tightly by any convenient method such as rubber bands. Remove any excess substrate at edges and from wrinkles by adjusting the substrate. Initially, apply 5 cc of water to the bioskin surface and 2 cc to the substrate. Once the Instron apparatus is in motion, apply an additional 10 cc of water with a syringe to the substrate. Place the sled on the bioskin and a place a 2,000 gram weight and activate the Instron apparatus. The tensile force is recorded continuously by a computer networked to the Instron. The friction force is measured as the average tensile force between 10 and 40 seconds of measurement. The Wet Friction Coefficient is calculated by dividing the friction force by the normal force, which is the sum of the 2,000 gram weight and the sled, the substrate typically adding negligible additional weight.

The second layer of the articles of the present invention preferably has a Wet Friction Coefficient of less than about 0.55 and more preferably of less than about 0.50. Furthermore, the additional layers of the present invention which are suitable for facilitating gripping of the article by the hand preferably have a Wet Friction Coefficient of greater than about 0.45, more preferably greater than about 0.55 and most preferably greater than about 0.65.

Absorptive Capacity "Tea Bag" Test

Absorptive Capacity can be determined by a gravimetric analytical technique using deionized water as the fluid for which Absorptive Capacity of the polymeric gelling agent is to be calculated. A sample of polymeric gelling agent is placed within a tea bag, immersed in an excess of deionized water for a specified period of time, and then centrifuged for a specific period of time. The ratio of polymeric gelling agent final weight after centrifuging minus initial weight (net fluid gain) to initial weight determines the Absorptive Capacity.

The following procedure is conducted under standard laboratory conditions at 23° C. (73° F.) and 50% relative humidity. Using a 6 cm×23 cm cutting die, the tea bag material is cut, folded in half lengthwise and sealed along two sides with a T-bar sealer to produce a 6 cm×6 cm tea bag square. The tea bag material utilized is a grade 1234 heat sealable material, obtainable from C. H. Dexter, Division of the Dexter Corp., Windsor Locks, Conn., U.S.A., or equivalent. Lower porosity tea bag material should be used if required to retain fine particles or fibers of polymeric gelling agent. 0.200 grams plus or minus 0.005 grams of the polymeric gelling agent is weighed onto a weighing paper and transferred into the tea bag and the top (open end) of the tea bag is sealed. An empty tea bag is sealed at the top and is used as a blank. Approximately 300 milliliters of deionized water are poured into a 1,000 milliliter beaker. The blank tea bag is submerged in the deionized water. The tea bag containing the polymeric gelling agent (the sample tea bag) is held horizontally to distribute the material evenly throughout the tea bag. The tea bag is laid on the surface of the deionized water. The tea bag is allowed to wet, for a period of no more than one minute, and then is fully submerged and soaked for 60 minutes. Approximately 2 minutes after the first sample is submerged, a second set of tea bags, prepared identically to the first set of blank and sample tea bags, is submerged and soaked for 60 minutes in the same manner as the first set. After the prescribed soak time has elapsed, for each set of tea bag samples, the tea bags are promptly removed (using tongs) from the deionized water. The samples are then centrifuged as described below. The centrifuge used is a Delux Dynac II Centrifuge, Fisher Model No. 05-100-26, obtainable from the Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0.238 cm) diameter circular holes equally spaced around the circumference of the outer wall, and having a basket floor with six ¼ inch (0.635 cm) diameter circular drainage holes equally spaced around the circumference of the basket floor at a distance of ½ inch (1.27 cm) from the interior surface of the outer wall to the center of the drainage holes, or an equivalent. The basket is mounted in the centrifuge so as to rotate, as well as brake, in unison with the centrifuge. The sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm, a timer is set for 3 minutes. After 3 minutes, the centrifuge is turned off and the brake is applied. The first sample tea bag and the first blank tea bag are removed and weighed separately. The procedure is repeated for the second sample tea bag and the second blank tea bag.

The Absorptive Capacity (AC) for each of the samples is calculated as follows: AC=(sample tea bag weight after centrifuge minus blank tea bag weight after centrifuge minus polymeric gelling agent weight)/(dry polymeric gelling agent). The Absorptive Capacity value for use herein is the average absorptive capacity of the two samples.

When an aqueous gel, hydrogel forming polymeric gelling agent, or an aqueous gellant material is used herein it is preferred that the material be able to absorb at least about 40 g water (deionized) per gram of gelling agent, preferably at least about 60 g/g, more preferably at least about 80 g/g.

Foamability Test

The Foamability Test measures the amount of lather generated by a cleansing article under simulated shower conditions (i.e., in the presence of running water).

The test is run with water with a hardness of 10 grains, a temperature of 104° F. and a water flow rate of 1.0 gallon per minute. The water is run through a sprinkler head which emits 16 individual streams of water within its 2 inch diameter. Place a plastic storage box measuring 23 inches length×16 inches width×9 inches height in a deep sink adjacent to the running water (e.g., Rubbermaid 14.7 gallon Storage Box). Then elevate one end of the storage box to create an angle of about 30 degrees, the slope running lengthwise. Cut away one side of the storage box in a semicircular pattern leaving a wall height of only 4" at the center to allow easy access. Place a flexible bath mat with suction feet, e.g., Rubbermaid Safti-Grip Bath Mat, faced down on the bottom of the storage box. Place an article of the present invention comprising a surfactant containing cleansing component in the center of the bath mat. If the article is flat in design, hold its leading edge up to allow wetting of the underside. Point the water at the article for 1–2 seconds to wet it, and then spray the water at the article as well as the surrounding mat to wet the article. Continue spraying the article for 5 seconds and then stop. A diverting lever to maintain flow but direct it through the shower head or towards the drain is useful. After the initial 1–2 seconds of wetting the article, an experimenter begins lathering the article vigorously at a stroke rate of 2 per second, dipping the article into the water trough at the bottom of the mat after each stroke to maintain a fully wet article and mat. Each stroke covers the entire distance, end-to-end, of the bath mat, reaching to each edge of the box. After 30 seconds total elapsed time (5 seconds with water spraying and 25 seconds without water spraying), repeat 30 second lathering cycle again. Then, remove the article from the tub without squeezing and place the article in a beaker. Remove the lather filled box from the sink and pour the box's contents through a cheesecloth covered colander (100% cotton, heavy duty cheesecloth, cut to about 16 inches×23 inches). Remove all of the lather and place in a suitable beaker for lather volume measurement while a catch basin under the colander catches the water which is then weighed to check the water flow rate. Carefully lift the cheesecloth out of the colander and transfer the foam to the previously filled foam containing beaker. Once all foam is transferred to the beaker, level the foam in the beaker and measure its volume. Then, measure the foam weight and calculate the density of the foam using its weight and volume. Next, return the box to the sink, and repeat the abovelisted steps with the previously used article. The total foam volume in the two minutes of lathering is the Foamability of the article. To ensure consistency, run a standard product at least at the start and end of each (daily) group of experiments. The standard product is the article of Example 1. The standard product typically produces an average of about 1250 ml of foam with a foam density of about 0.058 g/ml.

The articles of the present invention preferably produce from about 500 ml to about 4000 ml in 2 minutes, more preferably from about 750 ml to about 3000 ml and most preferably from about 1000 ml to about 2500 ml, of foam based on the Foamability Test.

Moisture Retention Methodology

As described above, the articles of the present invention are considered to be "substantially dry". As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The Moisture Retention is indicative of the dry feel that users perceive upon touching the articles of the present invention as opposed to the feel of "wet" wipes.

In order to determine the Moisture Retention of the present articles and other disposable substrate-based products, the following equipment and materials are needed.

| | |
|---|---|
| Bounty White Paper Towel | Procter & Gamble SKU 37000 63037 Basis Weight = 42.14 gsm |
| Balance | Accurate to 0.0 g |
| Lexan | 0.5" thickness large enough to cover samples completely and weighs 1000 g |
| Weight | A 2000 g weight or combination to equal 2000 g |

Next, weigh two paper towels separately and record each weight. Place one paper towel on flat surface (e.g. lab bench). Place the sample article on top of that towel. Place the other paper towel on top of sample article. Next, place the Lexan and then the 2000 g weight(s) on top of the sandwiched sample article. Wait 1 minute. After the minute, remove weight(s) and Lexan. Weigh the top and bottom paper towel and record the weight.

Calculate the Moisture Retention by subtracting the initial paper towel weight from the final weight (after 1 minute) for both the top and bottom paper towels. Add the weight differences obtained for the top and bottom paper towels. Assuming multiple articles are tested, average the total weight differences to obtain the Moisture Retention.

OPTIONAL COMPONENTS

The articles of the present invention may contain a variety of other components such as are conventionally used in a given product type provided that they do not unacceptably alter the benefits of the invention. These optional components should be suitable for application to human skin and hair, that is, when incorporated into the article they are suitable for use in contact with human skin without undue toxicity, incompatibility, instability, allergic response, and the like, within the scope of sound medical or formulator's judgment. The *CTFA Cosmetic Ingredient Handbook*, Second Edition (1992) describes a wide variety of nonlimiting cosmetic and pharmaceutical ingredients commonly used in the skin care industry, which are suitable for use in the articles of the present invention. Examples of these ingredient classes include: enzymes, abrasives, skin exfoliating agents, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, and the like). The articles of the present invention may include carrier components such as are known in the art. Such carriers can include one or more compatible liquid or solid filler diluents or vehicles which are suitable for application to skin or hair.

The articles of the present invention may optionally contain one or more of such optional components. Preferred articles optionally contain a safe and effective amount of an therapeutic benefit component comprising a therapeutic benefit agent selected from the group consisting of vitamin compounds, conditioning agents, skin treating agents, anti-acne actives, anti-wrinkle actives, anti-skin atrophy actives, anti-inflammatory actives, topical anesthetics, artificial tanning actives and accelerators, anti-microbial actives, anti-fungal actives, sunscreen actives, anti-oxidants, skin exfoliating agents, and combinations thereof. As used herein, "a safe and effective amount" means an amount of a compound or component sufficient to significantly induce a positive effect or benefit, but low enough to avoid serious side effects, (e.g., undue toxicity or allergic reaction), i.e., to provide a reasonable benefit to risk ratio, within the scope of sound medical judgment.

The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

Therapeutic Benefit Component

In certain embodiments of the present invention, the articles may optionally comprise a therapeutic benefit component. This benefit component is disposed adjacent to the water insoluble substrate and comprises from about 10% to about 1000%, more preferably, from about 10% to about 500%, and most preferably from about 10% to about 250%, by weight of the water insoluble substrate, of a therapeutic benefit agent. Preferably, the therapeutic benefit agent is selected from the group consisting of hydrophobic conditioning agents, hydrophilic conditioning agents, structured conditioning agents, and combinations thereof.

Hydrophobic Conditioning Agents

The articles of the present invention may comprise one or more hydrophobic conditioning agents which are useful for providing a conditioning benefit to the skin or hair during the use of the article. The articles of present invention preferably comprise from about 0.5% to about 1,000%, more preferably from about 1% to about 200%, and most preferably from about 10% to about 100%, by weight of the water insoluble substrate, of a hydrophobic conditioning agent.

The hydrophobic conditioning agent may be selected from one or more hydrophobic conditioning agents such that the weighted arithmetic mean solubility parameter of the hydrophobic conditioning agent is less than or equal to 10.5. It is recognized, based on this mathematical definition of solubility parameters, that it is possible, for example, to achieve the required weighted arithmetic mean solubility parameter, i.e., less than or equal to 10.5, for a hydrophobic conditioning agent comprising two or more compounds if one of the compounds has an individual solubility parameter greater than 10.5.

Solubility parameters are well known to the formulation chemist of ordinary skill in the art and are routinely used as a guide for determining compatibility's and solubilities of materials in the formulation process.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\Sigma_i E_i$=the sum of the heat of vaporization additive group contributions, and $\Sigma_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., *The Chemist's Companion*, John Wiley & Sons, pp. 456–463, (1972), which is incorporated by reference herein in its entirety.

Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp.47–69, which is incorporated by reference herein in its entirety.

Nonlimiting examples of hydrophobic conditioning agents include those selected from the group consisting of mineral oil, petrolatum, lecithin, hydrogenated lecithin, lanolin, lanolin derivatives, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and combinations thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

Lecithin is also useful as a hydrophobic conditioning agent. It is a naturally occurring mixture of the diglycerides of certain fatty acids, linked to the choline ester of phosphoric acid.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons. Polydecene, a branched liquid hydrocarbon, is also useful herein and is commercially available under the tradenames Puresyn 100® and Puresyn 3000® from Mobile Chemical (Edison, N.J.).

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, carpylic/capric triglyceride, PEG-6 caprylic/capric triglyceride, PEG-8 caprylic/capric triglyceride, and combinations thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Patent No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; each of which is incorporated by reference herein in its entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R_3SiO[R_2SiO]_x SiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x$ $[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810 ($C_{24}$–$C_{28}$ alkyl methicone) (sold by Goldschmidt) and SF1632 (cetearyl methicone)(sold by General Electric Company).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Hydrophobic chelating agents are also useful herein as hydrophobic conditioning agents. Suitable agents are described in U.S. Pat. No. 4,387,244, issued to Scanlon et al. on Jun. 7, 1983, and copending U.S. patent application Ser. Nos. 09/258,747 and 09/259,485, filed in the names of Schwartz et al. on Feb. 26, 1999.

Hydrophilic Conditioning Agents

The articles of the present invention may optionally comprise one or more hydrophilic conditioning agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the articles of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990, which is incorporated by reference herein in its entirety.

The therapeutic benefit component may be made into a variety of forms. In one embodiment of the present invention, the therapeutic benefit component is in the form of an emulsion. For instance, oil-in-water, water-in-oil, water-in-oil-in-water, and oil-in-water-in-silicone emulsions are useful herein. As used in the context of emulsions, "water" may refer not only to water but also water soluble or water miscible agents like glycerin.

Preferred therapeutic benefit components comprise an emulsion, which further comprises an aqueous phase and an oil phase. As will be understood by the skilled artisan, a given component will distribute primarily into either the aqueous or oil phase, depending on the water solubility/dispersibility of the therapeutic benefit agent in the component. In one embodiment, the oil phase comprises one or more hydrophobic conditioning agents. In another embodiment, the aqueous phase comprises one or more hydrophilic conditioning agents.

Therapeutic benefit components of the present invention, which are emulsion form, generally contain an aqueous phase and an oil or lipid phase. Suitable oils or lipids may be derived from animals, plants, or petroleum and may be natural or synthetic (i.e., man-made). Such oils are discussed above in the Hydrophobic Conditioning Agents section. Suitable aqueous phase components include the Hydrophilic Conditioning Agents, which are discussed above. Preferred emulsion forms include water-in-oil emulsions, water-in-silicone emulsions, and other inverse emulsions. Additionally, preferred emulsions also contain a hydrophilic conditioning agent such as glycerin such that a glycerin-in-oil emulsion results.

Therapeutic benefit components in emulsion form will preferably further contain from about 1% to about 10%, more preferably from about 2% to about 5%, of an emulsifier, based on the weight of therapeutic benefit component. Emulsifiers may be nonionic, anionic or cationic.

Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317–324 (1986). Therapeutic benefit components in emulsion form may also contain an anti-foaming agent to minimize foaming upon application to the skin. Anti-foaming agents include high molecular weight silicones and other materials well known in the art for such use.

The therapeutic benefit component may also be in the form of a microemulsion. As used herein, "microemulsion" refers to thermodynamic stable mixtures of two immiscible solvents (one apolar and the other polar) stabilized by an amphiphilic molecule, a surfactant. Preferred microemulsions include water-in-oil microemulsions.

Structured Conditioning Agents

The therapeutic benefit component may comprise structured conditioning agents. Suitable structured conditioning agents include, but are not limited to, vesicular structures such as ceramides, liposomes, and the like.

In another embodiment, the therapeutic benefit agents of the benefit component are comprised within a coacervate-forming composition. Preferably, the coacervate-forming composition comprises a cationic polymer, an anionic surfactant, and a dermatologically acceptable carrier for the polymer and surfactant. The cationic polymer may be selected from the group consisting of natural backbone quaternary ammonium polymers, synthetic backbone quaternary ammonium polymers, natural backbone amphoteric type polymers, synthetic backbone amphoteric type polymers, and combinations thereof.

More preferably, the cationic polymer is selected from the group consisting of natural backbone quaternary ammonium polymers selected from the group consisting of Polyquaternium-4, Polyquaternium-10, Polyquaternium-24, PG-hydroxyethylcellulose alkyldimonium chlorides, guar hydroxypropyltrimonium chloride, hydroxypropylguar hydroxypropyltrimonium chloride, and combinations thereof, synthetic backbone quaternary ammonium polymers selected from the group consisting of Polyquaternium-2, Polyquaternium-6, Polyquaternium-7, Polyquaternium-11, Polyquaternium-16, Polyquaternium-17, Polyquaternium-18, Polyquaternium-28, Polyquaternium-32, Polyquaternium-37, Polyquaternium-43, Polyquaternium-44, Polyquaternium-46, polymethacylamidopropyl trimonium chloride, acrylamidopropyl trimonium chloride/acrylamide copolymer, and combinations thereof; natural backbone amphoteric type polymers selected from the group consisting of chitosan, quaternized proteins, hydrolyzed proteins, and combinations thereof, synthetic backbone amphoteric type polymers selected from the group consisting of Polyquaternium-22, Polyquaternium-39, Polyquaternium-47, adipic acid/dimethylaminohydroxypropyl diethylenetriamine copolymer, polyvinylpyrrolidone/dimethylyaminoethyl methacyrlate copolymer, vinylcaprolactam/polyvinylpyrrolidone/dimethylaminoethylmethacrylate copolymer, vinaylcaprolactam/polyvinylpyrrolidone/dimethylaminopropylmethacrylamide terpolymer, polyvinylpyrrolidone/dimethylaminopropylmethacrylamide copolymer, polyamine, and combinations thereof; and combinations thereof. Even more preferably, the cationic polymer is a synthetic backbone amphoteric type polymer. Even still more preferably, the cationic polymer is a polyamine.

When the cationic polymer is a polyamine, it is preferred that the cationic polyamine polymer be selected from the group consisting of polyethyleneimines, polyvinylamines, polypropyleneimines, polylysines and combinations thereof. Even more preferably, the cationic polyamine polymer is a polyethyleneimine.

In certain embodiments in which the cationic polymer is a polyamine, the polyamine may be hydrophobically or modified. In this instance, the cationic polyamine polymer is selected from the group consisting of benzylated polyamines, ethoxylated polyamines, propoxylated polyamines, alkylated polyamines, amidated polyamines, esterified polyamines and combinations thereof. The coacervate-forming composition comprises from about 0.01% to about 20%, more preferably from about 0.05% to about 10%, and most preferably from about 0.1% to about 5%, by weight of the coacervate-forming composition, of the cationic polymer.

Suitable anionic surfactants include those discussed above as related to the "cleansing component." Preferably, for the coacervate-forming composition, the anionic surfactant is selected from the group consisting of sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isethionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

Suitable coacervate-forming compositions are further described in copending U.S. patent applications Ser. Nos. 09/397,747, filed in the name of Schwartz et al.; 09/397,746, filed in the name of Heinrich et al.; 09/397,712, filed in the name of Schwartz et al.; 09/397,723, filed in the name of Heinrich et al.; and 09/397,722, filed in the name of Venkitaraman et al.; each of which were filed on Sep. 16, 1999.

Alternatively, the coacervate-forming composition may comprise an anionic polymer, a cationic surfactant, and a dermatologically acceptable carrier for the polymer and surfactant. The anionic polymer may be selected from the group consisting of polyacrylic acid polymers, polyacrylamide polymers, copolymers of acrylic acid, acrylamide, and other natural or synthetic polymers (e.g., polystyrene, polybutene, polyurethane, etc.), naturally derived gums, and combinations thereof. Suitable gums include alginates (e.g., propylene glycol alginate), pectins, chitosans (e.g., chitosan lactate), and modified gums (e.g., starch octenyl succinate), and combinations thereof. More preferably, the anionic polymer is selected from the group consisting of polyacrylic acid polymers, polyacrylamide polymers, pectins, chitosans, and combinations thereof. Preferred articles of the present invention comprise from about 0.01% to about 20%, more preferably from about 0.05% to about 10%, and most preferably from about 0.1% to about 5%, by weight of the coacervate-forming composition, of the anionic polymer. Suitable cationic surfactants include, but are not limited to, those discussed herein.

The therapeutic benefit component of the article is suitable for providing therapeutic or aesthetic skin or hair benefits by deposition onto such surfaces of not only conditioning agents but also various agents including, but not limited to, anti-acne actives, anti-wrinkle actives, anti-microbial actives, anti-fungal actives, anti-inflammatory actives, topical anesthetic actives, artificial tanning agents and accelerators, anti-viral agents, enzymes, sunscreen actives, anti-oxidants, skin exfoliating agents, and combinations thereof.

It should also be understood that the therapeutic benefit component may be contained within the cleansing component of the present invention or vice versa such that they form a unitary component with indistinguishable ingredients.

Vitamin Compounds

The present articles may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

In particular, the articles of the present invention may comprise a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997) which is incorporated by reference herein in its entirety. The therapeutic component of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

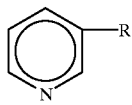

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

Skin Treating Agents

The articles of the present invention may contain one or more skin treating agents. Suitable skin treating agents include those effective for preventing, retarding, arresting, and/or reversing skin wrinkles. Examples of suitable skin treating agents include, but are not limited to, alpha-hydroxy acids such as lactic acid and glycolic acid and beta-hydroxy acids such as salicylic acid.

Anti-Acne Actives

Examples of anti-acne actives useful in the articles of the present invention include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of anti-wrinkle and anti-skin atrophy actives useful in the articles of the present invention include retinoic acid and its derivatives (e.g., cis and trans); retinol; retinyl esters; niacinamide, salicylic acid and derivatives thereof; sulfur-containing D and L amino acids and their derivatives and salts, particularly the N-acetyl derivatives, a preferred example of which is N-acetyl-L-cysteine; thiols, e.g., ethane thiol; hydroxy acids, phytic acid, lipoic acid; lysophosphatidic acid, and skin peel agents (e.g., phenol and the like).

Non-Steroidal Anti-Inflammatory Actives (NSAIDS)

Examples of NSAIDS useful in the articles of the present invention include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics

Examples of topical anesthetic drugs useful in the articles of the present invention include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Actives and Accelerators

Examples of artificial tanning actives and accelerators useful in the articles of the present invention include dihydroxyacetaone, tyrosine, tyrosine esters such as ethyl tyrosinate, and phospho-DOPA.

Antimicrobial and Antifungal Actives

Examples of antimicrobial and antifungal actives useful in the articles of the present invention include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Anti-viral Agents

The articles of the present invention may further comprise one or more anti-viral agents. Suitable anti-viral agents include, but are not limited to, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent applications Ser. Nos. 09/421,084 (Beerse et al.); 09/421,131 (Biedernann et al.); 09/420,646 (Morgan et al.); and 09/421,179 (Page et al.), which were each filed on Oct. 19, 1999.

Enzymes

The article of the present invention may optionally include one or more enzymes. Preferably, such enzymes are dermatologically acceptable. Suitable enzymes include, but are not limited to, keratinase, protease, amylase, subtilisin, etc.

Sunscreen Actives

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Hydrocolloids

Hydrocolloids may also be optionally included in the articles of the present invention. Hydrocolloids are well known in the art and are helpful in extending the useful life of the surfactants contained in the cleansing component of the present invention such that the articles may last throughout at least one entire showering or bathing experience. Suitable hydrocolloids include, but are not limited to, xanthan gum, carboxymethyl cellulose, hydroxyethyl cellulose, hydroxylpropyl cellulose, methyl and ethyl cellulose, natural gums, gudras guar gum, bean gum, natural starches, deionitized starches (e.g., starch octenyl succinate) and the like.

Exothermic Zeolites

Zeolites and other compounds which react exothermically when combined with water may also be optionally included in the articles of the present invention.

Hydrogel Forming Polymeric Gelling Agents

The articles of the present invention may optionally comprise an aqueous gel, i.e., a "hydrogel", formed from a hydrogel forming polymeric gelling agent and water. When an aqueous gel is present, the articles preferably comprise from about 0.1% to about 100%, by weight of the water insoluble substrate, more preferably from about 3% to about 50%, and most preferably from about 5% to about 35%, of a hydrogel forming polymeric gelling agent, calculated based on the dry weight of the hydrogel forming polymeric gelling agent.

In general, the hydrogel forming polymeric gelling agent materials of the present invention are at least partially crosslinked polymers prepared from polymerizable, unsaturated acid-containing monomers which are water-soluble or become water-soluble upon hydrolysis. These include monoethylenically unsaturated compounds having at least one hydrophilic radical, including (but not limited to) olefinically unsaturated acids and anhydrides which contain at least one carbon—carbon olefinic double bond. With respect to these monomers, water-soluble means that the monomer is soluble in deionized water at 25° C. at a level of at least 0.2%, preferably at least 1.0%.

Upon polymerization, monomeric units as described above will generally constitute from about 25 mole percent to 99.99 mole percent, more preferably from about 50 mole percent to 99.99 mole percent, most preferably at least about 75 mole percent of the polymeric gelling agent material (dry polymer weight basis), of acid-containing monomers.

The hydrogel forming polymeric gelling agent herein is partially crosslinked to a sufficient degree preferably that is high enough such that the resulting polymer does not exhibit a glass transition temperature (Tg) below about 140° C., and accordingly, the term "hydrogel forming polymeric gelling agent," as used herein, shall mean polymers meeting this parameter. Preferably the hydrogel forming polymeric gelling agent does not have a Tg below about 180° C., and more preferably does not have a Tg prior to decomposition of the polymer, at temperatures of about 300° C. or higher. The Tg can be determined by differential scanning calorimetry (DSC) conducted at a heating rate of 20.0° C./minute with 5 mg or smaller samples. The Tg is calculated as the midpoint between the onset and endset of heat flow change corresponding to the glass transition on the DSC heat capacity heating curve. The use of DSC to determine Tg is well known in the art, and is described by B. Cassel and M. P. DiVito in "Use of DSC To Obtain Accurate Thermodynamic and Kinetic Data", American Laboratory, January 1994, pp 14–19, and by B. Wunderlich in *Thermal Analysis*, Academic Press, Inc., 1990.

The hydrogel forming polymeric material is characterized as highly absorbent and able to retain water in its absorbed or "gel" state. Preferred hydrogel forming polymeric gelling agent hereof will be able to absorb at least about 40 g water (deionized) per gram of gelling agent, preferably at least about 60 g/g, more preferably at least about 80 g/g. These values, referred to as "Absorptive Capacity" herein can be determined according to the procedure in the Absorptive Capacity "Tea Bag" test described above.

The hydrogel forming polymeric gelling agent hereof will, in general, be at least partially crosslinked. Suitable cross-linking agents are well know in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages.

Cross-linking agents having at least two polymerizable double bonds include (i) di- or polyvinyl compounds such as divinylbenzene and divinyltoluene; (ii) di- or poly-esters of unsaturated mono- or poly-carboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or poly-allyl ethers of polyols; (vi) di- or poly-allyl esters of polycarboxylic acids such as diallyl phthalate, diallyl adipate, and the like; (vii) esters of unsaturated mono- or poly-carboxylic acids with mono-allyl esters of polyols such as acrylic acid ester of polyethylene glycol monoallyl ether; and (viii) di- or tri-allyl amine.

Cross-linking agents having at least one polymerizable double bond and at least one functional group reactive with the acid-containing monomer material include N-methylol acrylamide, glycidyl acrylate, and the like. Suitable cross-linking agents having at least two functional groups reactive with the acid-containing monomer material include glyoxal; polyols such as ethylene glycol and glycerol; polyamines such as alkylene diamines (e.g., ethylene diamine), poly-alkylene polyamines, polyepoxides, di- or polyglycidyl ethers and the like. Suitable polyvalent metal cross-linking agents which can form ionic cross-linkages include oxides, hydroxides and weak acid salts (e.g., carbonate, acetate and the like) of alkaline earth metals (e.g., calcium, magnesium) and zinc, including, for example, calcium oxide and zinc diacetate.

Cross-linking agents of many of the foregoing types are described in greater detail in Masuda et al., U.S. Pat. No. 4,076,663, issued Feb. 28, 1978, and Allen et al., U.S. Pat. No. 4,861,539, issued Aug. 29, 1989, both incorporated herein by reference. Preferred cross-linking agents include the di- or polyesters of unsaturated mono- or polycarboxylic acids mono-allyl esters of polyols, the bisacrylamnides, and the di- or tri-allyl amines. Specific examples of especially preferred cross-linking agents include N,N'-methylenebisacrylamide and trimethylol propane triacrylate.

The cross-linking agent will generally constitute from about 0.001 mole percent to 5 mole percent of the resulting hydrogel-forming polymeric material. More generally, the cross-linking agent will constitute from about 0.01 mole percent to 3 mole percent of the hydrogel-forming polymeric gelling agent used herein.

The hydrogel forming polymeric gelling agents hereof may be employed in their partially neutralized form. For purposes of this invention, such materials are considered partially neutralized when at least 25 mole percent, and preferably at least 50 mole percent of monomers used to form the polymer are acid group-containing monomers which have been neutralized with a base. Suitable neutralizing bases cations include hydroxides of alkali and alkaline earth metal (e.g. KOH, NaOH), ammonium, substituted ammonium, and amines such as amino alcohols (e.g., 2-amino-2-methyl-1,3-propanediol, diethanolamine, and 2-amino-2-methyl-1-propanol. This percentage of the total monomers utilized which are neutralized acid group-containing monomers is referred to herein as the "degree of neutralization." The degree of neutralization will preferably not exceed 98%.

Hydrogel forming polymeric gelling agents suitable for use herein are well known in the art, and are described, for example, in U.S. Pat. No. 4,076,663, Masuda et al., issued Feb. 28, 1978; U.S. Pat. No. 4,062,817, Westerman, issued Dec. 13, 1977; U.S. Pat. No. 4,286,082, Tsubakimoto et al., issued Aug. 25, 1981; U.S. Pat. No. 5,061,259, Goldman et al., issued Oct. 29, 1991, and U.S. Pat. No. 4,654,039, Brandt et al., issued Mar. 31, 1987 each of which is incorporated herein in its entirety.

Hydrogel forming polymeric gelling agents suitable for use herein are also described in U.S. Pat. No. 4,731,067, Le-Khac, issued Mar. 15, 1988, U.S. Pat. No. 4,743,244, Le-Khac, issued May 10, 1988, U.S. Pat. No. 4,813,945, Le-Khac, issued Mar. 21, 1989, U.S. Pat. No. 4,880,868, Le-Khac, issued Nov. 14, 1989, U.S. Pat. No. 4,892,533, Le-Khac, issued Jan. 9, 1990, U.S. Pat. No. 5,026,784, Le-Khac, issued Jun. 25, 1991, U.S. Pat. No. 5,079,306, Le-Khac, issued Jan. 7, 1992, U.S. Pat. No. 5,151,465, Le-Khac, issued Sep. 29, 1992, U.S. Pat. No. 4,861,539, Allen, Farrer, and Flesher, issued Aug. 29, 1989, and U.S. Pat. No. 4,962,172, Allen, Farrer, and Flesher, issued Oct. 9, 1990, each of which is incorporated herein by reference in its entirety.

Suitable hydrogel forming polymeric gelling agents in the form of particles are commercially available from Hoechst Celanese Corporation, Portsmouth, Va., USA (Sanwet™ Superabsorbent Polymers) Nippon Shokubai, Japan (Aqualic™, e.g., L-75, L-76) and Dow Chemical Company, Midland, Mich., USA (Dry Tech™).

Hydrogel forming polymeric gelling agents in the form of fibers are commercially available from Camelot Technologies Inc., Leominster, Mass., USA (Fibersorb™, e.g., SA 7200H, SA 7200M, SA 7000L, SA 7000, and SA 7300).

The articles of the present invention may also contain other hydrophilic gelling agents. These include carboxylic acid-containing polymers as otherwise described above, except which have relatively lower degrees of crosslinking, such that they exhibit a Tg below 140° C., as well as a variety of other water soluble or colloidally water soluble polymers, such as cellulose ethers (e.g. hydroxyethyl cellulose, methyl cellulose, hydroxy propylmethyl cellulose), polyvinylpyrrolidone, polyvinylalcohol, guar gum, hydroxypropyl guar gum and xanthan gum. Preferred among these additional hydrophilic gelling agents are the acid-containing polymers, particularly carboxylic acid-containing polymers. Especially preferred are those that comprise water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95 to 99 weight percent of an olefinically unsaturated carboxylic monomer selected from the group consisting of acrylic, methacrylic and ethacrylic acids; about 1 to about 3.5 weight percent of an acrylate ester of the formula:

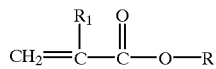

wherein R is an alkyl radical containing 10 to 30 carbon atoms and $R_1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of crosslinking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

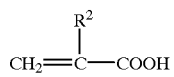

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent.

The second monomeric ingredient useful in the production of these carboxylic polymers are the polyalkenyl polyethers having more than one alkenyl ether grouping per molecule, such as alkenyl groups in which an olefinic double bond is present attached to a terminal methylene grouping, $CH_2$=C<.

The additional monomeric materials which may be present in the polymers include polyfunctional vinylidene monomers containing at least two terminal $CH_2$< groups, including for example, butadiene, isoprene, divinyl benzene, divinyl naphthlene, allyl acrylates, and the like. These polymers are fully described in U.S. Pat. No. 2,798,053, to Brown, issued Jul. 2, 1957, which is incorporated herein by reference in its entirety.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, acrylates/C10–30 alkyl acrylate cross polymer (available as Carbopol 934, Carbopol 941, Carbopol 950, Carbopol 951, Carbopol 954, Carbopol 980, Carbopol 981, Carbopol 1342, and the Pemulen series, respectively, from B.F. Goodrich).

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by Lipo Chemicals Inc. under the trademark of HYPAN hydrogels. These hydrogels consist of crystalline plicks of nitrates on a C—C backbone with various other pendant groups such as carboxyls, amides, and amidines. An example would include HYPAN SA 100 H, a polymer powder available from Lipo Chemical.

Neutralizing agents for use in neutralizing the acidic groups of these polymers include those previously described.

Cationic Surfactants

Cationic surfactants are typically categorized as non-lathering surfactants but may be used in the articles of the present invention provided they do not negatively impact the desired benefits of the articles.

Nonlimiting examples of cationic surfactants useful herein are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of cationic surfactants useful herein include cationic alkyl ammonium salts such as those having the formula:

wherein $R_1$, is selected from an alkyl group having from about 12 to about 18 carbon atoms, or aromatic, aryl or alkaryl groups having from about 12 to about 18 carbon atoms; $R_2$, $R_3$, and $R_4$ are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO$—$(CH_2)_n$—, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

Chelators

The articles of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime and derivatives thereof.

Flavonoids

The articles of the present invention may optionally comprise a flavonoid compound. Flavonoids are broadly disclosed in U.S. Pat. Nos. 5,686,082 and 5,686,367, both of which are herein incorporated by reference. Flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof Most preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., a glycoside, an ester or an ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

Sterols

The articles of the present invention may comprise a safe and effective amount of one or more sterol compounds. Examples of useful sterol compounds include sitosterol, stigmasterol, campesterol, brassicasterol, lanosterol, 7-dehydrocholesterol, and mixtures thereof. These can be synthetic in origin or from natural sources, e.g., blends extracted from plant sources (e.g., phytosterols).

Anti-Cellulite Agents

The articles of the present invention may also comprise a safe and effective amount of an anti-cellulite agent. Suitable agents may include, but are not limited to, xanthine compounds (e.g., caffeine, theophylline, theobromine, and aminophylline).

Skin Lightening Agents

The articles of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof, e.g., magnesium ascorbyl phosphate or sodium ascorbyl phosphate or other salts of ascorbyl phosphate. Skin lightening agents suitable for use herein also include those described in copending patent application Ser. No. 08/479,935, filed on Jun. 7, 1995 in the name of Hillebrand, corresponding to PCT Application No. U.S. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 3, 1995, published Sep. 8, 1995.

Binders

The articles of the present invention may optionally comprise binders. Binders or binding materials are useful for sealing the various layers of the present articles to one another thereby maintaining the integrity of the article. The binders may be in a variety of forms including, but not limited to, spray on, webs, separate layers, binding fibers, etc. Suitable binders may comprise latexes, polyamides, polyesters, polyolefins and combinations thereof.

METHODS OF MANUFACTURE

The cleansing articles of the present invention are manufactured by adding the cleansing component to the appropriate sheet of the first layer via a conventional method which may include, but is not limited to, spraying, slot coating, and roll transfer (e.g., pressure roll). The sheet of the second layer is then placed on the sheet of the first layer over the cleansing component. The sheets are sealed together by a conventional sealing method which may include, but is not limited to, heat, pressure, glue, ultrasound, etc. The sealed sheets are then partitioned into units for the consumer's use. Optional manufacturing steps may include calendaring to flatten the article as well as drying.

METHODS OF CLEANSING AND DELIVERING A THERAPEUTIC OR AESTHETIC BENEFIT AGENT TO THE SKIN OR HAIR

The present invention also relates to a method of cleansing the skin or hair with a cleansing article of the present invention. These methods comprise the steps of: a) wetting with water a disposable cleansing article comprising a water insoluble substrate comprising 1) an apertured first layer having a water flux rate of from about 0.4 $cm^3/cm^2$-s to about 20 $cm^3/cm^2$-s and 2) a second layer attached to the first 1a cleansing component comprising one or more surfactants, said component being disposed adjacent to the substrate and b) contacting the skin or hair with the wetted article. In other embodiments, the present invention is also useful for delivering various therapeutic or aesthetic benefit agents to the skin or hair wherein the method further comprises the step of contacting the skin or hair with an article comprising at least two layers with a benefit agent component disposed between the two layers.

The articles of the present invention are intended to be wetted with water prior to use. The article is wetted by immersion in water or by placing it under a stream of water. When the articles of the present invention comprise a lathering surfactant in the cleansing component, lather may be generated from the article by mechanically agitating and/or deforming the article either prior to or during contact of the article with the skin or hair. The resulting lather is useful for cleansing the skin or hair. During the cleansing process and subsequent rinsing with water, any therapeutic or aesthetic benefit agents are deposited onto the skin or hair. Deposition of the therapeutic or aesthetic benefit agents are enhanced by the physical contact of the substrate with the skin or hair as well by the inclusion of one or more deposition aids.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

1. CLEANSING COMPONENTS

Example 1

Prepare a representative cleansing component for the articles of the present invention in the following manner.

Shave a 53.0 gms of a bar soap which includes the following components:

| Component | Wt % |
|---|---|
| Sodium Cocyl Isethionate | 27.77 |
| Paraffin | 16.72 |

-continued

| Component | Wt % |
|---|---|
| Sodium Alkyl Glycerol Sulfonate (AGS) | 14.90 |
| Soaps | 11.41 |
| Glycerine | 8.57 |
| Water | 5.50 |
| Stearic Acid | 5.74 |
| Sodium Isethionate | 3.04 |
| NaCl | 1.41 |
| EDTA | 0.10 |
| Etidronic Acid | 0.10 |
| Polyox | 0.03 |
| Perfume | 0.70 |
| Miscellaneous (including pigments) | 4.01 |
| Total | 100 |

Mix the bar soap shavings with 37.0 gms glycerin (99.7%), 9.5 gms water, and 0.5 gms perfume. Heat mixture to 200° F. while stirring continuously. Cold-mill mixture on a standard 3-roll mill and store cleansing component in a suitable sealed container.

Example 2

Prepare a representative cleansing component for the articles of the present invention in the following manner.

Shave 40.0 gms of a bar soap which includes the following components:

| Component | Wt % |
|---|---|
| Sodium Soap | 52.40 |
| Sodium Alkyl Glycerol Sulfonate (AGS) | 16.50 |
| Magnesium Soap | 13.40 |
| Glycerine | 0.19 |
| Water | 5.50 |
| Stearic Acid | 1.60 |
| Sodium Isethionate | 3.00 |
| NaCl | 3.89 |
| EDTA | 0.10 |
| Etidronic Acid | 0.10 |
| Perfume | 0.70 |
| Miscellaneous (including pigments) | 2.62 |
| Total | 100 |

Mix the bar soap shavings with 45.0 gms glycerin (99.7%), 4.5 gms water, and 0.5 gms perfume. Heat mixture to 200° F. while stirring continuously. Cold-mill mixture on a standard 3-roll mill and store cleansing component in a suitable sealed container.

Example 3

A representative powdery cleansing component for the articles of the present invention is prepared in the following manner.

Shave 40.0 gms of a bar soap which includes the following components:

| Component | Wt % |
|---|---|
| Soap (Magnesium and Sodium) | 80.16 |
| Water | 11.50 |
| Stearic Acid | 5.70 |

| Component | Wt % |
|---|---|
| NaCl | 1.10 |
| EDTA | 0.25 |
| Perfume | 1.15 |
| Miscellaneous (including pigments) | 0.14 |
| Total | 100 |

Store the bar soap flakes in a suitable sealed container.

Example 4

A representative cleansing component for the articles of the present invention is prepared in the following manner.

Shave 40.0 gms of a bar soap which includes the following components:

| Component | Wt % |
|---|---|
| Sodium Soap | 74.20 |
| Water | 24.00 |
| NaCl | 0.65 |
| EDTA | 0.18 |
| Perfume | 0.16 |
| Miscellaneous (including pigments) | 0.81 |
| Total | 100 |

Blend the bar soap flakes with sodium bicarbonate in a 90:10 weight ratio. Mill the mixture twice in a standard 3-roll mill. Collect flakes and store in a suitable sealed container.

Example 5

A representative cleansing component is prepared in the following manner.

Blend 180 grams of the cleansing component of Example 1 with 12 grams of a hydrogel forming polymeric gelling agent (also referred to as an absorbent gellant material or AGM). The AGM should not swell in the mixture but provides the advantage of swelling during use in the shower to create a 3-dimensional volume which makes a thin substrate feel like a thicker washing cloth.

Example 6

A representative cleansing component is prepared in the following manner.

Blend the cleansing component of Example 2 with a 0.1%, by weight of the bar soap flakes, of a protease enzyme. Next, blend resultant mixture with 2%, by weight of the cleansing component, of dry hydrocolloid, sodium carboxymethylcellulose and mill. Store the enzyme cleansing component in a suitable a sealed container.

Example 7

A representative cleansing component is prepared in the following manner.

Blend the cleansing component of Example 1 with 1%, by weight of the of the cleansing component, of xanthan gum and cold-mill the mixture twice on a standard 3-roll benchtop mill. Once milled, store the cleansing component in a suitable sealed container.

Example 8

Prepare a representative cleansing component which includes the following components.

| Component | Wt % |
|---|---|
| Decylpolyglucose | 12.0 |
| Cocamidopropyl betaine | 12.0 |
| Sodium lauroyl sarcosinate | 12.0 |
| Butylene glycol | 3.6 |
| PEG 14M | 1.8 |
| Polyquaternium-10 | 0.9 |
| Dex panthenol | 0.7 |
| Phenoxyethanol | 0.5 |
| Benzyl alcohol | 0.5 |
| Methylparaben | 0.45 |
| Propylparaben | 0.25 |
| Disodium EDTA | 0.2 |
| Water | 55.1 |

Example 9

Prepare a representative cleansing component which includes the following components.

| Component | Wt % |
|---|---|
| Triethanolamine | 2.9 |
| Polyquaternium-39 | 0.1 |
| Monolauryl phosphate | 4.0 |
| C12-C14N-methyl Glucose amide[1] | 5.0 |
| Cocamidopropylhydroxysultaine[2] | 2.0 |
| Sodium decyl sulfate | 0.5 |
| Citric acid monohydrate | 0.3 |
| Perfume, Preservatives & misc. | 4.0 |
| Water | 81.2 |

[1]Available from Hoechst Celanese
[2]Available from Rhone Poulenc

Add ingredients slowly in the following order at 60° C. until each is dissolved in the water: TEA, lauryl phosphate, glucose amide. Cool to 45° C. and add sultaine, polyquaternium-39 and sulfate, stirring as before. Add perfume, preservatives and cool to room temperature.

Example 10

Prepare a representative tear-free liquid cleansing component which includes the following components.

| Component | Wt % |
|---|---|
| Cocamido propyl betaine | 17.1 |
| Sodium trideceth sulfate | 8.3 |
| POE 100 sorbitan monooleate | 7.5 |
| Misc. (including perfume, preservative, dye) | 2.0 |
| Water | 65.1 |

Distinguishing characteristics of this composition are its non-irritating properties to skin and eyes.

II. SKIN MOISTURIZATION COMPONENTS

Example 11

A representative skin moisturization component is prepared in the following manner.

| | |
|---|---|
| SEFA coffonate | 57.5 grams |
| Elvax 40W (ethylene vinyl acetate) | 8.0 grams |
| Tospearl 145A | 20.0 grams |
| Perfume | 1.0 grams |
| Anhydrous citric acid | 0.3 grams |
| Empigen BS 98 (betaine) | 3.75 grams (80% active) |
| Hainposyl L 95 (sarcosinate) | 9.47 grams (95% active) |

Melt the Elvax into the SEFA cottonate at 90° C. and mix. Add the powders and mix again. Cool mixture to 40° C. and then add perfume. Store mixture in a suitable sealed container.

Example 12

Prepare a representative skin conditioning component which includes the following components.

| Component | WT % |
|---|---|
| Polydimethylsiloxane, 500 cSt fluid | 6.7 |
| Polydimethylsiloxane, gum | 5.9 |
| Stearyl methicone wax | 9.3 |
| Polybutene | 5.0 |
| Tocopherol | 1.5 |
| Cyclomethicone | 31.5 |
| Stearyl alcohol | 25.5 |
| Glyceryl stearate | 2.6 |
| Glycerin | 3.0 |
| Nonylphenol polyglycine ether[1] | 5.0 |
| Micronized titanium dioxide | 1.0 |
| Octyl methoxycinnamate | 2.0 |
| Fragrance & misc. | 1.0 |

[1]Available as Hamplex TNP, Hampshire Chemical Co.

Heat the silicone fluid to 65° C., stir in the polyglycine ether, inorganic sunscreen, stearyl alcohol, glyceryl stearate, polybutene, silicone gum and wax. Mix until homogeneous. Blend separately the cyclomethicone, Fragrance, vitamin and glycerin. Add these while cooling to room temperature. Store composition in a sealed jar until ready to add to an article.

Example 13

Prepare a representative skin conditioning component which includes the following components.

| STEP | Component | WT % |
|---|---|---|
| 1 | Combine the following with heat and agitation until melted and homgeneous at 70–75° C. | |
| | PEG 30 dipolyhydroxystearate[1] | 3.0 |
| | SEFA Cottonate[2] | 25.0 |
| | Petrolatum | 4.0 |
| | Tribehenin | 5.0 |
| | C10–C30 Cholesterol/Lanosterol esters | 13.0 |

-continued

| STEP | Component | WT % |
|---|---|---|
| 2 | Heat the following to 75° C. | |
| | Glycerin | 50.0 |
| 3 | Slowly add glycerin to lipid phase while homogenizing using Ultra Turrax T-25 mixer with super fine head. Cool composition using water bath and gentle stirring to 45° C. | |

[1] Available as Arlacel P135 from ICI
[2] SEFA is an acronym for Sucrose Esters of Fatty Acids, which are fully esterified

Example 14

Prepare a representative skin conditioning component which includes the following components.

| Component | WT % |
|---|---|
| Hydrophobic Phase: | |
| Isohexadecane | 19.0 |
| Lecithin, purified[1] | 10.3 |
| Hydrophilic Phase: | |
| Glycerin | 18.7 |
| Propylene glycol | 18.7 |
| Gellant: | |
| Carnauba wax | 33.3 |

[1] Available as Epikuron 200 from Lucas Meyer

Prepare a microemulsion by blending together all ingredients at room temperature except the gellant until a transparent composition is obtained Add gellant and heat carefully while stirring until the gellant melts and blends with the composition. Cool rapidly.

Example 15

Prepare a representative skin conditioning component which includes the following components.

| Part A | Wt % |
|---|---|
| Sodium lauroyl sarosinate[1] | 8.87 |
| Polethyleneimine[2] | 7.39 |
| Water | 4.43 |
| Sulfuric acid | 6.36 |
| Fragrance, misc. | |
| Glycerin | 34.45 |
| Propylene glycol | 2.50 |
| Part B - Polymer gelling agent | |
| Polyacrylamide and isoparaffin[3] | 16.0 |
| Part C - Physical gelling agents | |
| 12-Hydroxystearic acid | 12.0 |
| Carnauba wax | 4.0 |
| Stearyl alcohol | 4.0 |

[1] Available as Hamposyl L-95 from Hampshire Chemical, dry
[2] Available as Epomin SP-018, molecular weight about 1800, from Nippon Shokubai Co.
[3] Available as Sepigel 305 from Seppic Corp.

Blend part A except the cationic polymer with heat to about 65° C. until homogeneous. Maintaining heat, blend in the physical gelling agents. Cool to 45° C. and add the cationic polymer. Blend in the polymer gelling agent and continue cooling to room temperature.

III. ARTICLES

Example 16

A representative cleansing article is prepared in the following manner.

Prepare an apertured first layer by sealing an 8"×9" cellulosic, 2-ply, embossed paper towel having high wet strength (e.g., Bounty Rinse & Re-Use) (as disclosed in U.S. Pat. Nos. 4,529;480 and 4,637,859) to a 8"×9" sheet of microapertured 100 mesh formed film (e.g., as disclosed in U.S. Pat. No. 4,629,643) by heating the edges with an impulse sealer until the thermoplastic is fully bonded to the cellulosic towel. Seal the first layer with the surface aberrations (i.e., the male side) facing away from the cellulosic substrate.

Prepare the second layer by sealing a 8"×9" sheet of the same type of cellulosic towel as the first layer to a sheet of formed film having hydroformed 100 mesh microapertures in one direction and macroapertures in the opposite direction. Seal the second layer with the surface aberrations (i.e., the male side) of the macroapertures against the cellulosic substrate.

Add 20 grams of the cleansing component of Example 2 to the exposed, male side of the microapertured film of the first layer in four equal quadrants (i.e., 5 gms in the center of each quadrant). Lay the second layer over the cleansing component and first layer with the cellulosic sheet of the second layer facing toward the cleansing component. Next, flatten, smooth and seal each edge of the layers with an impulse sealer. Trim and round the substrate corners. Make seals across the center of the substrate in each direction, dividing the article into quadrants. Flatten the cleansing component in the center of the article with a hand-held rolling device to form an article which generates greater than about 2000 ml of foam in 2 minutes in the Foamability Test.

Example 17

A representative multiple chambered cleansing article is prepared in the following manner.

Prepare a cleansing article as outlined in Example 16 except rather than add the cleansing component of Example 2 add 5 grams of the cleansing component of Example 1 in each of the first and fourth quadrants (diagonally opposed) and add 5 grams of the cleansing component of Example 7 in each of the second and third quadrants to form an article which generates greater than about 2000 ml of foam in 2 minutes in the Foamability Test.

Example 18

A representative cleansing article is prepared in the following manner.

Prepare a cleansing article as outlined in Example 16 except rather than adding the cleansing component of Example 2 add 12 grams of the powdery cleansing component of Example 3, dividing it equally into the quadrants before sealing.

Example 19

A representative cleansing article is prepared in the following manner.

Prepare an apertured first layer by laying an 8"×6" formed film sheet having 0.55 mm apertures with the male side up onto a flat silicone rubber sheet. Place a sheet of microapertured 100 mesh formed film with the male side of the apertures up on top of the first formed film sheet. Hold edges of both formed films in place temporarily.

Prepare the second layer in the same manner as the first layer using the same materials. Tack the edges of the second layer materials with a heat sealing die that utilizes a pressure-plate heat sealing device (e.g., Sentinel Model 808 heat sealer commercially available from Sencorp of Hyannis, Mass.). Add 115 grams of the cleansing component of Example 1 to the interior surface of the first layer. Lay the interior surface of the second layer on the cleansing component with the male side of the formed film of the second layer facing toward the cleansing component. Place the layers on the bottom plate of the heat sealing dye. Heat the top plate which is prepared to seal in an hourglass shape of about 6 inches long and 3.5 inches wide with a narrowed waist of 2.5 inches. Carefully position the cleansing component carefully such that it is contained by the seal and will not interfere with the sealed edge. Position a release film between the layers and the heated plates. Seal the edges using 30 psi supply pressure at 260° F set point for a sealing time of 3 seconds. Remove the resultant article and trim its edges. Affix a hanging cord to the end of the article to form an article which generates about 2000 ml of foam in 2 minutes in the Foamability Test.

Example 20

A representative cleansing article is prepared in the following mannner.

Prepare a cleansing article as outlined in Example 19 except the second layer is prepared using a formed film which is both microapertured and macroapertured with the male side of the microapertures facing out and the female side of the macroapertures facing out.

Example 21

A representative cleansing and skin care article is prepared in the following manner.

Prepare the apertured first layer by adhering a soft, adhesive bonded nonwoven cloth with basis weight of about 84 gsm and water flux of about 1.9 $cm^3/cm^2$-s (commercially available as "Scott Shop Rags") to a layer of microapertured 100 mesh formed film with its male side facing away from the nonwoven cloth, using a continuous coating of contact cement. Cut out a 6" square section. Add two 4 gm strips of the cleansing component of Example 2 along two parallel sides, a minimum of ¼ inch from the edges to allow room for sealing. Add a 4 gm strip of the enzyme containing cleansing component of Example 6 to the center of the cloth such that it is parallel to the previously added cleansing component strips.

Prepare a second layer by laying a sheet of microapertured 100 mesh formed film, male side facing down over the entire first layer. Place a sheet of 0.55 mm apertured formed film, male side facing down, on top of the microapertured 100 mesh formed film of the second layer. Seal the edges and two strips parallel to the cleansing component with the impulse sealer. Trim the article edges and round the corners. Affix a strap to the back of the article to the nonwoven side with a hot melt adhesive to form an article which effectively lathers for an entire shower, cleansing the entire body, and leaves the skin moisturized and soft.

Example 22

A representative cleansing and moisturizing article is prepared in the following manner.

Place the first layer of Example 16 on a flat silicone rubber sheet. Add 4 grams of the skin moisturization component of Example 11 to the center of the first layer. Add 20 grams of the cleansing component of Example 7 in a ring-shaped strip to the outside portion of the first layer. Place the second layer of Example 16 on top of the first layer. Place the layers as well as the silicone sheet on the bottom plate of an impulse sealer. Heat the top plate which is prepared to seal in an hourglass shape of about 6 inches long and 3.5 inches wide with a narrowed waist of 2.5 inches. Carefully position the cleansing component carefully such that it is contained by the seal and will not interfere with the sealed edge. Position a release film between the layers and the heated plates. Seal the edges using 30 psi supply pressure at 260 set point for a sealing time of 3 seconds. Remove the resultant article and seal the edges in a 7"×9" rectangular pattern. Trim the edges and round the corners of the article to form an article which effectively lathers for an entire shower, cleansing the entire body, and leaves the skin moisturized by deposition of the hydrophobic active material in effective amounts.

Example 23

A representative cleansing and moisturizing article is prepared in the following manner.

Place the first layer of Example 16 on a flat silicone rubber sheet. Add 20 grams of the cleansing component of Example 1 to the center of four quadrants of the sheet, dividing the weight equally (i.e., 5 gMs per quadrant). Place a sheet of microapertured 100 mesh formed film over the first layer with the male side facing the cleansing component. Permanently affix the layers to one another by sealing the edges as well as across the article in a cross pattern using the impulse sealer. The resultant article is about 7"×9". Place the article back on the silicone rubber sheet facing in the same direction and add 5 grams of the skin moisturization component of Example 11 to the center. Place an additional layer of microapertured 100 mesh formed film over the article with the male side facing the skin moisturization component. Place a sheet of formed film having hydroformed 100 mesh microapertures in one direction and macroapertures in the opposite direction with the microapertures facing up, as the top layer. Place the article and additional layer on the bottom plate of an impulse sealer. Place a release film between the article/additional layer and the heated plates. Seal the additional layer to the article only around the skin moisturization component in an hourglass shape at a 20 psi supply pressure, 260° F. for a sealing time of 2 seconds. The resulting seal contains the skin moisturization component in a sleeve located over part of the balance of the article. Seal the outside edges of the article and trim to form an article which effectively lathers for an entire shower, cleansing the entire body, and leaves the skin moisturized by deposition of the hydrophobic active material in effective amounts.

Example 24

A cleansing and moisturizing kit is prepared in the following manner.

Prepare the cleansing article of Example 16. Prepare a skin moisturization article utilizing the first and second layers of Example 16 and substituting 5 grams of the skin moisturization component of Example 11 for the cleansing component. Package the first cleansing article and the moisturization article together. Upon use, the skin or hair is cleansed with the cleansing article in the shower or bath. Rinse the skin or body. Moisturize the skin while still wet with the moisturization article.

Example 25

A cleansing and drying kit is prepared in the following manner.

Prepare the cleansing article of Example 16. Prepare a drying article by removing the inner liner from a Pampers Premium disposable diaper and cutting a 7-inch long elliptically shaped section of fibrous matte, absorbent gellant material and backsheet (collectively known as the absorbent core). Place a sheet of formed film having hydroformed 100 mesh microapertures in one direction and macroapertures in the opposite direction with the microapertures facing up, as the top layer. Seal the edges of the top layer to the backsheet with an impulse sealer and trim the edges. Package the cleansing article and drying article together.

Example 26

A cleansing, moisturizing and drying kit is prepared in the following manner.

Prepare the cleansing article of Example 16. Prepare a drying and moisturizing article as follows. Place a mixture of 1 gm of hydrogel forming polymeric gelling agent (also known as absorbent gellant material or AGM) and 3 gms of petrolatum between two sheets of microapertured 100 mesh formed film with the male sides facing the mixture. Place a sheet of formed film having hydroformed 100 mesh microapertures in one direction and macroapertures in the opposite direction with the microapertures facing up as an additional layer. Place the sheets and additional layer on the bottom plate of the impulse sealer such that the sealer will form a seal around the moisturization component in the shape of an hourglass. Place a release film between the sheets/additional layer and heated plates. Seal with 20 psi supply pressure, 260 degrees Fahrenheit temperature, and for a sealing time of 3 seconds. Cut away the excess 100 mesh microapertured film sheets such that a microapertured pocket is affixed to the larger film. Remove the inner liner from a Pampers Premium disposable diaper and cut a 7-inch long elliptically shaped section of fibrous matte, AGM and backsheet. Position pocketed layers over the fibrous matte with the pocket to the interior side and seal the edges with an impulse sealer and trim to smooth. Package the cleansing and moisturizing and drying articles together.

Use the cleansing article to lather and cleanse in the shower or bath. Next, use the drying article to effectively dry the skin in place of a towel while simultaneously applying a moisturizer to the skin or hair.

Example 27

A representative two-step, two-in-one cleansing and moisturizing kit is prepared in the following manner.

Prepare the cleansing article of Example 16. Affix an hourglass-shaped sheet of impermeable, opaque, white polyethylene in the center of the article to the cellulosic towel-containing exterior surface of the article's outermost portion using an impulse sealer. Next, cut a second, matching hourglass shaped sheet of transparent polyethylene film, leaving a tab at one end. Then, prepare a gel by mixing 2 gms glycerin, 1 gm sucrose octaester of cottonseed oil fatty acids, 0.6 gms sucrose behenate, 1 gm aromatic eucalyptus oil, 0.01 grams of FD&C Blue dye, 0.5 grams Tospearl 145A and heat to 200° F. Cool the mixture to 90° F. and stir in 2 gms glycerin and 0.045 gms protease enzyme (i.e., 0.1%, by weight of the cleansing component). Add the gel to the top of the opaque polyethylene film. Then, affix the hourglass shaped transparent film over the gel using a pressure sensitive adhesive. The two-step kit may be used to first cleanse the skin or hair in the shower or bath. The article may then be turned over, the tab removed, and the article may be used to apply the gel to the leg area. The gel is then rinsed away, leaving the entire body cleansed and the leg areas moisturized and treated.

Example 28

A cleansing and moisturizing skin care article is prepared in the following manner.

Place a sheet of micro- and macroapertured formed film having hydroformed 100 mesh microapertures in the opposite direction of its macroapertures, with microapertures facing up. Prepare a 10% dispersion in water of 4 parts octaester of cottonseed oil fatty acids, I part sucrose behenate, and 2 parts petrolatum by melting these hydrophobic components together. Next, blend these hydrophobic components with hot water and immediately spray the formed film sheet to make a moisturizing film. Upon drying, the add-on weight of the sprayed formed film should be about 60 grams per square meter. Then, prepare the skin cleansing article of Example 16, substituting the moisturizing film for the outermost apertured film of Example 16 to form an article which effectively lathers in the shower or bath while the hydrophobic skin benefit agents on the exterior of the article deposit sufficient material on the skin or hair to leave it feeling moisturized.

Example 29

A representative cleansing article is prepared in the following manner.

Prepare a stretchable, elastic formed film by stretching a 100 mesh, hydroapertured formed film between grooved plates as described in Example 1 of U.S. Pat. No. 5,518,801 (Chappell, et al.). The resulting deformed film exhibits significant z-direction caliper and a soft feel as a result of the stretching. Then prepare a cleansing article as outlined in Example 16 above, substituting the stretchable, elastic formed film for the micro- and macroapertured film layer which is on the exterior side of the article. The cleansing article has a soft feel.

Example 30

A representative cleansing article is prepared in the following manner.

Prepare two stretchable, elastic formed films as outlined in Example 29. Then, prepare the article of Example 16, substituting the two stretchable films for both of the formed film sheets of Example 16, the microapertured sheet and the micro- and macroapertured sheets. The cleansing article has a soft, thick feel.

Example 31

A representative car cleansing article is prepared in the following manner.

Blend 50.0 grams of liquid car wash concentrate (e.g., "Armor All"™ or other car wash concentrate which contains a surfactant, e.g., alkyl aryl sulfonate) with 5 grams of a hydrogel forming polymeric gelling agent (AGM). Dry the mixture in a convection oven at 45° C. for 24 hours, stirring occasionally. Once a gelled paste forms, spread the paste between a first layer and a second layer of a microapertured, formed film having hydroformed 100 mesh microapertures. Then, divide a diaper core containing airlaid cellulose batting and AGM and place it on the exterior surfaces of the first layer and the second layer with the layers extending beyond the edges of the batting. Add two additional layers to exterior surface of the exterior surface of the diaper core material such that the additional layers extend beyond the batting. The first laid additional layer is the formed film disclosed in U.S. Pat. No. 4,342,314, with male apertures facing the batting. The second laid additional layer is a microapertured and macroapertured formed film disclosed in U.S. Pat. No. 4,629,643, with microapertures facing male side to the exterior of the article, and macroapertures in the opposite direction.

Prepare an additional layer to be placed on the side of the article opposite the first two additional layer by laminating with adhesive the formed film disclosed in U.S. Pat. No. 4,342,314, to a layer of adhesively bonded synthetic nonwoven having a basis weight of about 84 gsy and a Water Flux Rate of about 1.9 $cm^3/cm^2$-s, with the male side facing the nonwoven. Place the laminate against the cellulose batting with the nonwoven side facing the outermost portion of the article. Seal the edges with an impulse sealer and trim. The article measures about 8 inches by 6 inches and weighs 29.2 grams and is suitable to cleanse an entire automobile by wetting with water and scrubbing. The article does not scratch the exterior of the automobile in the presence of dirt when the formed film is used as the scrubbing side; and is easily rinsed to rinse off when it gets dirty, without washing away the surfactant.

Example 32

Prepare a representative cleansing article in the following manner.

An apertured first layer is prepared which is a vacuum formed laminate of a formed film comprising low density polyethylene and having about 290 vacuum formed apertures per square centimeter, and a fibrous nonwoven with a basis weight about 15 gsm comprising 20 micron polyester fibers. The layer has a water flux of about 10 $cm^3/cm^2$-s. The cleansing component of Example 8 is hot extruded in lines onto the film side of the vacuum formed laminate in rows about 1 inch apart to achieve about 4 grams of surfactant composition per finished article. A layer of the apertured first layer is cut to a size of 6 inches by 10 inches. A layer of 2 oz/sq yd polyester batting cut to the same size is placed over the surfactant coated side of the first layer. The polyester batting has a basis weight of 2 oz/yd$^2$ and is comprised of a blend of fibers of about 23 microns and 40 microns average diameter, at least some of which are crimped. The thickness of the batting is about 0.23 in. measured at 5 gsi. The batting is believed to be heat-bonded, utilizing no adhesive. The batting layer is sealed to the apertured first layer in the shape of a mitt, open at one end, by sealing the edges using a heat sealing die and a pressure-platen heat sealing device such as a Sentinel Model 808 heat sealer available from Sencorp, Hyannis, Mass. The edges are trimmed and the article is ready for use.

Example 33

Prepare a representative cleansing article in the following manner.

An apertured first layer is prepared which is a formed film comprising low density polyethylene (LLDPE) having about 65 vacuum formed apertures per square centimeter and a water flux of about 12.8 $cm^3/cm^2$-s. Surfactant is coated onto one the male protruding side of the formed film in the same manner as described in Example 32. A layer of a batting which is a 4 oz/sq yd polyester is placed over the surfactant coated side of the apertured first layer. The polyester batting has a basis weight of 4 oz/yd$^2$ and is comprised of polyester fibers of about 30 microns average diameter and is adhesive bonded, available for example as Mountain Mist Extra Heavy Batting #205 from Steams Textiles, Cincinnati, Ohio. A cellulose layer is placed on the remaining exposed side of the apertured first layer. The layers are prepared as a mitt in the same manner as previously described.

Example 34

Prepare a representative cleansing article in the following manner.

A layer of very soft batting comprising a homogeneous blend of crimped, 3 denier sheath-core bicomponent fibers having a polyethylene outer sheath surrounding a PET core and 8 denier hollow PET fibers, and having a basis weight of about 49 gsm is dipped in the surfactant composition of Example 9 until it absorbs 10 grams of the composition within the fiber interstices, and the composition is dried. The batting has a thickness of about 97 mils measured at 30 gsi, a machine direction tensile strength of about 1350 grams per linear inch and an absorbent capacity of about 1750%, prior to coating. An apertured first layer which is a formed film which is a 50/50 LDPE/HDPE blend with an internal black mesh scrim is placed against one side of the batting. The formed film has about 10 apertures per square centimeter and a water flux of about 17.3 $cm^3/cm^2$-s. The formed film is sealed to the batting in a 2 inch square grid using an impulse bar sealer. A third layer which is a fibrous nonwoven is placed against the formed film. The nonwoven is spunlace blend of 70% rayon and 30% PET fibers, bonded with a styrene-butadiene adhesive, which is hydroapertured to form holes about 2 mm in diameter and having a basis weight of about 70 gsm. The layers are prepared in an oval shaped article measuring about 10 inches by 7 inches with rounded corners, by sealing the edges and 3 points in the center of the article using a heat sealing die and a pressure-platen heat sealing device such as a Sentinel Model 808 heat sealer available from Sencorp, Hyannis, Mass. The edges are trimmed and the article is ready for use.

Example 35

Prepare a representative cleansing and conditioning article in the following manner.

The article of Example 34 is prepared except the batting used is comprised of 3-denier bicomponent fibers and has a thickness of 79 mils measured at 30 gsi, and a basis weight of about 50 gsm. Prior to sealing the article, a rupturable packet is prepared and sealed into the article in the following manner. A rupturable packet is prepared using a polymer coated foil film sealed with 3 strong seals at 3 edges and a fourth weaker seal along one edge. The packet measures about 1.25 inches by 2.0 inches and is filled with 3.5 grams of the skin care composition of Example 13 prior to sealing the final edge. The packet is ruptured by the user of the article, requiring only light hand pressure to do so. The edges of the foil packet are rounded. The rupturable packet is placed onto a piece of a 3 mil thick white polyethylene film which measures about 2.5 inches square, and sealed to the fibrous nonwoven described in Example 34. The fibrous nonwoven is then sealed to the other side of the article of Example 34 in the same manner as previously described, making sure the sealing dots in the article center do not contact the rupturable packet.

Example 36

Prepare a representative cleansing article in the following manner.

A layer of very soft batting comprising a homogeneous blend of crimped, 3 denier sheath-core bicomponent fibers having a polyethylene outer sheath surrounding a PET core and 8 denier hollow PET fibers, and having a basis weight of about 49 gsm is dipped in the surfactant composition of Example 10 until it absorbs 10 grams of the composition within the fiber interstices, and the composition is dried. The batting has a thickness of about 97 mils measured at 30 gsi, a machine direction tensile strength of about 1350 grams per linear inch and an absorbent capacity of about 1750%, prior to coating. An apertured first layer which is a formed film which is a white 50/50 LDPE/HDPE blend vacuum formed in a thick honeycomb patter. The formed film has about 10 apertures per square centimeter and a water flux of about 15.3 $cm^3/cm^2$-s. The formed film is sealed to the batting in a 2 inch square grid using an impulse bar sealer. A third layer which is a fibrous nonwoven is placed against the formed film. The nonwoven is spunlace blend of 70% rayon and 30% PET fibers, bonded with a styrene-butadiene adhesive, which is hydroapertured to form holes about 2 mm in diameter and having a basis weight of about 70 gsm. The layers are prepared in an oval shaped article measuring about 10 inches by 7 inches with rounded corners by sealing the edges and 3 points in the center of the article using a heat sealing die and a pressure-platen heat sealing device such as a Sentinel Model 808 heat sealer available from Sencorp, Hyannis, Mass. The edges are trimmed and the article is ready for use.

Example 37

Prepare a representative cleansing and conditioning article in the following manner.

The article of Example 35 is prepared except that 3.5 grams of the skin care composition of Example 12 is used in the rupturable packet.

Example 38

Prepare a representative cleansing and conditioning article in the following manner.

The article of Example 35 is prepared except that 3.5 grams of the skin care composition of Example 14 is used in the rupturable packet.

Example 39

Prepare a representative cleansing and conditioning article in the following manner.

The cleansing mitt of Example 32 is prepared. Four grams of the skin benefit composition of Example 12 is slot coated evenly onto the surfaces of the article by heating the composition and pumping it through a narrow slit dye, across which the mitt is dragged. Both surfaces of the article are coated. The article is cooled in a refrigerator to solidify the conditioning composition and packaged until ready for use.

What is claimed is:

1. A disposable cleansing article comprising:
   a) a water insoluble substrate comprising:
      1) an apertured first layer wherein said first layer has a water flux rate of from about 0.4 $cm^3/cm^2$-s to about 20 $cm^3/cm^2$-s;
      2) a second layer attached to said first layer; and
   b) from about 0.5% to about 3,000%, by weight of the substrate, of a cleansing component comprising at least about 1 gram, of a lathering surfactant, said cleansing component being positioned between said first layer and said second layer of said substrate.

2. The article of claim 1 wherein first layer has at least about 1 aperture/$cm^2$.

3. The article of claim 1 wherein said first layer is a selected from the group consisting of formed films and formed film composite materials.

4. The article of claim 1 wherein said second layer is selected from the group consisting of nonwovens, wovens, sponges, polymeric netted meshes, formed films, and combinations thereof.

5. The article of claim 4 wherein said second layer is a nonwoven selected from the group consisting of cellulosic fibers, synthetic fibers, formed films, and combinations thereof.

6. The article of claim 5 wherein said second layer is a formed film which is macroapertured.

7. The article of claim 1 wherein said second layer has a water flux rate of from about 5 $cm^3/cm^2$-s to about 120 $cm^3/cm^2$.

8. The article of claim 1 wherein said second layer is a selected from the group consisting of formed films and formed film composite materials.

9. The article of claim 8 wherein said second layer has at least about 1 aperture/$cm^2$.

10. The article of claim 1 that further comprises one or more additional layers.

11. The article of claim 1 that further comprises an additional layer having a thickness of at least 1 millimeter.

12. The article of claim 10 wherein said additional layer is selected from foam, corrugated materials, macroscopically expanded materials, and combinations thereof.

13. The article of claim 12 wherein said macroscopically expanded materials are selected from the group consisting of embossed materials, debossed materials, and combinations thereof.

14. The article of claim 1 which exhibits a flux differential (or gradient) of at least 2.5 $cm^3/cm^2$-s between said first layer and said second layer.

15. A method of cleansing the skin and hair which comprises the steps of:
    a) wetting with water the article of claim 1; and
    b) contacting the skin or hair with the wetted article.

16. A disposable cleansing article comprising:
    a) a water insoluble substrate comprising:
       1) an apertured first layer having an exterior surface and an interior surface wherein said first layer comprises a formed film and said first layer has a water flux rate of from about 0.4 $cm^3/cm^2$-s to about 20 $cm^3/cm^2$-s;
       2) a second layer having an exterior surface and an interior surface wherein said second layer comprises a formed film and wherein said second layer is positioned adjacently to said first layer;
       3) a third layer comprising cellulosic fibers, said third layer being positioned adjacently to said exterior surface of said first layer; and
    b) a cleansing component comprising a surfactant, said component being disposed adjacent to the substrate.

17. A disposable cleansing article comprising:
a) a water insoluble substrate comprising:
1) an apertured first layer wherein said first layer has a water flux rate of from about 0.4 cm$^3$/cm$^2$-s to about 20 cm$^3$/cm$^2$-s and has at least about 1 aperture/cm$^2$;
2) a second layer attached to said first layer;
b) a cleansing component comprising a surfactant, said component disposed adjacent to said substrate; and
c) a therapeutic benefit component disposed adjacent to said substrate.

18. A method of cleansing and therapeutically treating the skin and hair, said method comprising the steps of:
a) wetting with water the article of claim 17 and
b) contacting the skin or hair with the wetted article.

19. A cleansing kit comprising the article of claim 1.

20. A substantially dry, water-activated, disposable personal care cleansing article comprising:
a) a water insoluble substrate comprising:
1) an apertured first layer selected from the group consisting of formed films and formed film composite materials, wherein said first layer has a water flux rate of from about 0.4 cm$^3$/cm$^2$-s to about 20 cm$^3$/cm$^2$-s;
2) a second layer attached to said first layer, wherein said second layer is a nonwoven selected from the group consisting of cellulosic fibers, synthetic fibers, formed films, and combinations thereof; and
b) from about 0.5% to about 3,000%, by weight of the substrate, of a cleansing component comprising at least about 1 gram, by weight of the substrate, of a lathering surfactant, said cleansing component being positioned between said first layer and said second layer of said substrate.

* * * * *

UNITED STATES PATENT AND TRADEMARK OFFICE
CERTIFICATE OF CORRECTION

PATENT NO.     : 6,491,928 B1
DATED          : December 10, 2002
INVENTOR(S)    : E. D. Smith, III It is certified that error appears in the above-identified patent and that said Letters Patent is hereby corrected as shown below:

Column 15,
Line 46, "alkylirinoacetates" should read -- alkyliminoacetates --.

Column 35,
Line 19, "Biedernann" should read -- Biedermann --.

Column 37,
Line 56, "bisacrylamnides" should read -- bisacrylamides --.

Column 42,
Line 65, "thereof" should read -- thereof. --.

Column 44,
Line 19, "la" should read -- layer; and a --.

Column 46,
Line 57, "a sealed" should read -- sealed --.

Column 48,
Line 48, "Fragrance" should read -- fragrance --.

Column 56,
Line 8, "Steams" should read -- Stearns --.

Signed and Sealed this

Eleventh Day of March, 2003

JAMES E. ROGAN
*Director of the United States Patent and Trademark Office*